(12) United States Patent
Nishio et al.

(10) Patent No.: US 8,192,963 B2
(45) Date of Patent: Jun. 5, 2012

(54) BACTERIUM CAPABLE OF PRODUCING L-AMINO ACID AND METHOD FOR PRODUCING L-AMINO ACID

(75) Inventors: Yousuke Nishio, Kawasaki (JP); Yoshihiro Usuda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/037,772

(22) Filed: Mar. 1, 2011

(65) Prior Publication Data

US 2011/0201062 A1 Aug. 18, 2011

(30) Foreign Application Priority Data

Sep. 5, 2008 (JP) ................................ 2008-228859

(51) Int. Cl.
C12P 13/14 (2006.01)
C12P 13/10 (2006.01)
C12P 13/08 (2006.01)
(52) U.S. Cl. ......................... 435/110; 435/114; 435/115
(58) Field of Classification Search .................. 435/110, 435/114, 115
See application file for complete search history.

(56) References Cited

U.S. PATENT DOCUMENTS

| | | |
|---|---|---|
| 6,911,332 B2 | 6/2005 | Usuda et al. |
| 7,026,149 B2 | 4/2006 | Usuda et al. |
| 7,029,893 B2 | 4/2006 | Usuda et al. |
| 7,060,475 B2 | 6/2006 | Usuda et al. |
| 7,192,748 B2 | 3/2007 | Usuda et al. |
| 7,220,570 B2 | 5/2007 | Usuda et al. |
| 7,306,933 B2 | 12/2007 | Van Dien et al. |
| 7,468,262 B2 | 12/2008 | Usuda et al. |
| 7,695,946 B2 | 4/2010 | Usuda et al. |
| 7,696,315 B2 | 4/2010 | Usuda et al. |
| 7,833,761 B2 | 11/2010 | Terashita et al. |
| 2005/0233308 A1 | 10/2005 | Nishio et al. |
| 2009/0093029 A1 | 4/2009 | Usuda et al. |
| 2009/0148915 A1 | 6/2009 | Van Dien et al. |
| 2009/0203090 A1 | 8/2009 | Ptitsyn et al. |
| 2009/0239269 A1 | 9/2009 | Tajima et al. |
| 2009/0246835 A1 | 10/2009 | Iwatani et al. |
| 2009/0291478 A1 | 11/2009 | Usuda et al. |
| 2010/0047878 A1 | 2/2010 | Nagai et al. |
| 2010/0062497 A1 | 3/2010 | Shiraga et al. |
| 2010/0081180 A1 | 4/2010 | Fukui et al. |
| 2010/0093044 A1 | 4/2010 | Terashita et al. |
| 2010/0112647 A1 | 5/2010 | Hara et al. |
| 2010/0221792 A1 | 9/2010 | Nagai et al. |
| 2011/0014663 A1 | 1/2011 | Suzuki et al. |

FOREIGN PATENT DOCUMENTS

| | | |
|---|---|---|
| JP | 2010-183841 | 8/2010 |
| WO | WO2007/100009 | 9/2007 |

OTHER PUBLICATIONS

*Escherichia coli* K-12 substr. MG1655 Polypeptide: putative transcriptional regulator LysR-type, Accession Nos. G6737 (EcoCyc), b1422, ECK1416, (2011).
Keseler, I. M., et al., "EcoCyc: a comprehensive database resource for *Escherichia coli*," Nucleic Acids Res. 2005;33:D334-D337.
Riley, M., et al., "*Escherichia coli* K-12: a cooperatively developed annotation snapshot-2005," Nucleic Acids Res. 2006;34(1):1-9.
International Preliminary Report on Patentability for PCT Patent App. No. PCT/JP2009/065426 (Apr. 12, 2011).
Baba, T., et al., "Construction of *Escherichia coli* K-12 in-frame single-gene knockout mutants: the Keio collection," Mol. Sys. Biol. 2006;2:1-11.
Database GenoBase [online], [retrieved on Oct. 1, 2009], http://ecoli.naist.jp/GB6/info.jsp?id=JW5226> ECK No. ECK1416, Gene name: ycdI, Description: predicted DNA-binding transcriptional regulator.
International Search Report for PCT Patent App. No. PCT/JP2009/065426 (Oct. 13, 2009).

*Primary Examiner* — Tekchand Saidha
(74) *Attorney, Agent, or Firm* — Shelly Guest Cermak; Cermak Nakajima LLP

(57) ABSTRACT

A bacterium is described which belongs to the Enterobacteriaceae family, and has an ability to produce an L-amino acid, such as L-glutamic acid, L-arginine and L-threonine. The bacterium is modified so that the activity of a protein encoded by ydcI gene is decreased, thereby producing and accumulating the L-amino acid selected from L-glutamic acid, L-arginine, and L-threonine in the culture medium or cells of the bacterium when cultured in a culture medium. Subsequently, the L-amino acid is collected from the culture medium or the bacterium.

6 Claims, No Drawings

BACTERIUM CAPABLE OF PRODUCING L-AMINO ACID AND METHOD FOR PRODUCING L-AMINO ACID

This application is a Continuation of, and claims priority under 35 U.S.C. §120 to, International Application No. PCT/JP2009/065426, filed Sep. 3, 2009, and claims priority therethrough under 35 U.S.C. §119 to Japanese Patent Application No. 2008-228859, filed Sep. 5, 2008, the entireties of which are incorporated by reference herein. Also, the Sequence Listing on compact disk filed herewith is hereby incorporated by reference (File name: 2011-03-01T_US-459_Seq_List; File size: 55 KB; Date recorded: Mar. 1, 2011).

BACKGROUND OF THE INVENTION

1. Field of the Invention

The present invention relates to a method of producing an L-amino acid selected from L-glutamic acid, L-arginine and L-threonine using a microorganism. L-glutamic acid and L-arginine are industrially useful as seasonings. L-threonine is useful for feed materials.

2. Brief Description of the Related Art

L-amino acids are typically produced industrially by fermentation methods in which a variety of microorganisms are used. For example, for the production of L-glutamic acid, coryneform L-glutamic acid-producing bacteria mainly belonging to the genus *Brevibacterium, Corynebacterium* or *Microbacterium* or mutant strains thereof are used (Akashi, K. et al, Amino Acid Fermentation. Japan Scientific Societies Press, p. 195 to 215, 1986). Other microorganisms which can be used to produce L-glutamic acid by fermentation include microorganisms belonging to the genus *Bacillus, Streptomyces, Penicillium* or the like (Japanese Laid-Open Patent Publication No. 5-244970); microorganisms belonging to the genus *Pseudomonas, Arthrobacter, Serratia, Candida* or the like (U.S. Pat. No. 3,563,857); microorganisms belonging to the genus *Bacillus, Pseudomonas* or *Serratia, Aerobacter aerogenes* (currently *Enterobacter aerogenes*) or the like (Japanese Patent Publication (Kokai) No. 32-9393); or an *Escherichia coli* mutant strain or the like (Japanese Laid-Open Patent Publication No. 5-244970). In addition, microorganisms belonging to the genus *Klebsiella, Erwinia, Pantoea* or *Enterobacter* can also be used to produce L-glutamic acid by fermentation (Laimonis A. Laimins, Proc. Natl. Acad. Sci. USA, 1978 July; 75 (7): 3216-19; Laimonis A. Laimins, Proc. Natl. Acad. Sci. USA, 1981 January; 78 (1): 464-68; Mark O. Waldethaug, J. Bacteriol., 1992 April; 174 (7):2152-59).

In order to produce a substance of interest, such as an L-amino acid, by fermentation using the above-mentioned microorganisms, for example, wild-type microorganisms (wild-type strain), or auxotrophic strains derived from a wild-type strain, metabolic regulation mutant strains derived from a wild-type strain, such as a drug-resistant mutant strain, or a method in which a strain having both characteristics of autotrophic strain and metabolic regulation mutant strain can be used.

Furthermore, in recent years, recombinant DNA technology has been employed in fermentation production of a substance of interest. For example, L-amino acid productivity of a microorganism is improved by enhancing the expression of a gene encoding an L-amino acid biosynthetic enzyme (U.S. Pat. No. 5,168,056 and U.S. Pat. No. 5,776,736), or by enhancing the influx of a carbon source into the L-amino acid biosynthetic pathway (U.S. Pat. No. 5,906,925).

On the basis of sequence analyses and the like, the protein YdcI, which has been reported to be native to bacteria of the Enterobacteriaceae family, including *Escherichia coli*, is presumed to be a LysR-type transcription factor (Keseler, I. M. et al., "EcoCyc: A comprehensive database resource for *Escherichia coli*." Nucleic Acids Res. 2005, Vol. 33, D334-337; Encyclopedia of *Escherichia coli* K-12 Genes and Metabolism, [online], [searched on Apr. 12, 2007], Internet <URL://ecocyc.org/>). In *Escherichia coli*, YdcI is encoded by the ydcI gene (Riley, M. et al., "*Escherichia coli* K-12: a cooperatively developed annotation snapshot-2005", Nucleic Acids Res. 2006, Vol. 34, 1-9). Production of L-lysine, L-threonine, and L-tryptophan using a bacterium in which ydcI gene is enhanced has been reported (Japanese Patent Application No. 2007-141802); however, for L-threonine, this patent document does not demonstrate the effect of a strain in which the ydcI gene is amplified. There has also been no report of L-amino acid production using an ydcI gene-deficient bacterium.

SUMMARY OF THE INVENTION

An aspect of the present invention is to provide a bacterium belonging to the Enterobacteriaceae family which is capable of efficiently producing an L-amino acid such as L-glutamic acid, L-arginine and L-threonine; and to provide a method of efficiently producing the aforementioned L-amino acid using the bacterium.

It has been found that production of L-glutamic acid, L-arginine, and L-threonine in bacterium can be improved by attenuating expression of the ydcI gene encoding a protein which is presumed to be a LysR-type transcription factor.

It is an aspect of the present invention to provide a bacterium belonging to the Enterobacteriaceae family that is able to produce an L-amino acid selected from the group consisting of L-glutamic acid, L-arginine, L-threonine, and combinations thereof, and said bacterium is modified so that the activity of a protein encoded by ydcI gene is attenuated as compared to an unmodified bacterium.

It is another aspect of the present invention to provide the bacterium as described above, wherein the activity of the protein encoded by ydcI gene is attenuated by decreasing the expression of the ydcI gene or by disrupting the ydcI gene.

It is another aspect of the present invention to provide the bacterium as described above, wherein the protein encoded by ydcI gene is selected from the group consisting of: A) a protein comprising the amino acid sequence shown in SEQ ID NO: 2, 12 or 14; and B) a protein comprising the amino acid sequence shown in SEQ ID NO: 2, 12 or 14, except that one or several amino acids are substituted, deleted, inserted or added, and wherein said protein has DNA binding activity.

It is another aspect of the present invention to provide the bacterium as described above, wherein said ydcI gene is selected from the group consisting of:

(a) a DNA comprising the nucleotide sequence shown in 301-1221 of SEQ ID NO: 1, 301-1230 of SEQ ID NO: 11 or 301-1218 of SEQ ID NO: 13; and (b) a DNA which hybridizes under stringent conditions with a DNA comprising the nucleotide sequence shown in 301-1221 of SEQ ID NO: 1, 301-1230 of SEQ ID NO: 11 or 301-1218 of SEQ ID NO: 13, or with a probe which can be prepared from the same nucleotide sequence, said DNA encoding a protein having DNA binding activity.

It is another aspect of the present invention to provide the bacterium as described above, wherein said bacterium belongs to the genus *Escherichia, Enterobacter* or *Pantoea*.

It is another aspect of the present invention to provide a method of producing an L-amino acid selected from the group consisting of L-glutamic acid, L-arginine and L-threonine, comprising A) culturing the bacterium as described above in a medium to allow the L-amino acid to be produced and accumulated in the medium or bacterium; and B) collecting the L-amino acid from the medium or the bacterium.

DESCRIPTION OF THE PREFERRED EMBODIMENTS

<1> Bacterium of the Present Invention

The bacterium as described by the presently disclosed subject matter is a bacterium which belongs to the Enterobacteriaceae family, is able to produce an L-amino acid, such as L-glutamic acid, L-arginine, and L-threonine, and is modified so that the activity of a protein encoded by the ydcI gene is attenuated.

The phrase "is able to produce an L-amino acid such as L-glutamic acid, L-arginine and L-threonine" refers to the ability of the bacterium to, when cultured in a medium, produce and cause accumulation of the aforementioned L-amino acid(s) in the medium or bacterial cells such that the L-amino acid(s) can be recovered from the medium or bacterial cells. The bacterium can be able to produce L-glutamic acid, L-arginine, or L-threonine, and can produce two or more of these L-amino acids in combination. The bacterium can inherently be able to produce the aforementioned L-amino acid(s); however, the bacterium can also be modified by mutagenesis or by recombinant DNA technology so that the bacterium acquires the ability to produce the aforementioned L-amino acid(s).

<1-1> Imparting the Ability to Produce an L-Amino Acid

Hereinafter, a method of imparting to the bacterium the ability to produce an L-amino acid such as L-glutamic acid, L-arginine, and L-threonine, is described. Also, the bacteria which can be used in this method are also described. However, any method or bacteria can be used as long as the ability to produce the aforementioned L-amino acid is retained.

The bacterium is not particularly restricted as long as it belongs to the Enterobacteriaceae family which can include bacteria of the genera *Escherichia, Enterobacter, Pantoea, Klebsiella, Serratia, Erwinia, Salmonella* and *Morganella*, and is able to produce the aforementioned L-amino acid. Specifically, bacteria belonging to the Enterobacteriaceae family based on the classification described in the NCBI (National Center for Biotechnology Information) database (www.ncbi.nlm.nih.gov/Taxonomy/Browser/wwwtax. cgi?id=91347) can be employed. Particular examples of the parent strain of the Enterobacteriaceae bacterium which can be used for modification can include bacteria belonging to the genus *Escherichia, Enterobacter* or *Pantoea*.

*Escherichia* bacteria that can be used to obtain the *Escherichia* bacterium are not particularly restricted; however, specifically, bacteria described by Neidhardt et al. (Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, D.C.) can be used. Examples of the bacteria described therein include *Escherichia coli*. Specific examples of bacterial strains include *Escherichia coli* W3110 (ATCC 27325) and *Escherichia coli* MG1655 (ATCC 47076), both of which originate from the prototype wild-type K12 strain.

These bacterial strains can be obtained from, for example, the American Type Culture Collection (address: P.O. Box 1549, Manassas, Va. 20108, 1, United States of America). That is, each bacterial strain is given a unique accession number, and can be ordered according to this accession number (see www.atcc.org/). The accession numbers for each bacterial strain are listed in the catalog of the American Type Culture Collection.

Examples of bacteria belonging to the genus *Enterobacter* include *Enterobacter agglomerans* and *Enterobacter aerogenes*. It is noted here, however, that certain strains of *Enterobacter agglomerans* were recently re-classified as *Pantoea agglomerans, Pantoea ananatis* or *Pantoea stewartii* on the basis of nucleotide sequencing and the like of their 16S rRNA. As long as the bacterium is classified in the Enterobacteriaceae family, the bacterium can belong to either the genus *Enterobacter* or *Pantoea*.

Furthermore, bacteria belonging to the genus *Pantoea, Erwinia*, or *Enterobacter* can be classified as γ-proteobacteria and are taxonomically very closely related (J Gen Appl Microbiol 1997 December; 43 (6) 355-361, International Journal of Systematic Bacteriology, October 1997, p 1061-1067). In recent years, based on the DNA-DNA hybridization experiments and the like, some bacteria belonging to the genus *Enterobacter* have been re-classified as *Pantoea agglomerans* or *Pantoea dispersa* (International Journal of Systematic Bacteriology, July 1989; 39 (3). p. 337-345). Furthermore, some bacteria belonging to the genus *Erwinia* have been re-classified as *Pantoea ananas* or *Pantoea stewartii* (see International Journal of Systematic Bacteriology, January 1993; 43 (1), p. 162-173).

As the *Enterobacter* bacterium, specifically, those strains exemplified in EP 952221 A can be used.

Examples of a representative strain of the genus *Enterobacter* include *Enterobacter agglomerans* ATCC12287.

Examples of a representative bacterial strain of the genus *Pantoea* include *Pantoea ananatis, Pantoea stewartii, Pantoea agglomerans*, and *Pantoea citrea*. Specific examples thereof include the following strains:

*Pantoea ananatis* AJ13355 strain (FERM BP-6614) (EP 0952221 A)

*Pantoea ananatis* AJ13356 strain (FERM BP-6615) (EP 0952221 A)

*Pantoea ananatis* AJ13601 strain (FERM BP-7207) (EP 0952221 A)

These strains were originally identified as *Enterobacter agglomerans* when they were isolated, and deposited as *Enterobacter agglomerans*; however, as described in the above, they were re-classified as *Pantoea ananatis* on the basis of nucleotide sequencing and the like of their 16S rRNA.

Examples of bacteria belonging to the genus *Erwinia* include *Erwinia amylovora* and *Erwinia carotovora*, and examples of bacteria belonging to the genus *Klebsiella* include *Klebsiella planticola*. Specific examples thereof include the following strains:

*Erwinia amylovora* ATCC15580 strain

*Erwinia carotovora* ATCC15713 strain

*Klebsiella planticola* AJ13399 strain (FERM BP-6600) (EP 955368 A)

*Klebsiella planticola* AJ13410 strain (FERM BP-6617) (EP 955368 A)

The method of imparting the ability to produce the aforementioned L-amino acid to the aforementioned bacteria belonging to the Enterobacteriaceae family, and a method of enhancing the ability to produce the aforementioned L-amino acid in such bacteria will now be described.

In order to impart L-amino acid-producing ability, methods can be used which have been conventionally employed in breeding a coryneform bacterium or *Escherichia* bacterium, for example, acquisition of an auxotrophic mutant strain, analog-resistant strain, or metabolic regulation mutant strain, and creation of a recombinant strain in which the expression of enzyme(s) of the L-amino acid biosynthetic pathway is enhanced (see Amino Acid Fermentation. Japan Scientific Societies Press, first edition issued on May 30, 1986: p 77-100). In the breeding of an L-amino acid-producing bacterium, the characteristics such as auxotrophy, analog-resistance, and metabolic regulation mutation can be imparted individually, or two or more thereof can be imparted in combination. In addition, the expression of the L-amino acid biosynthetic enzymes can be enhanced individually, or two or more thereof can be enhanced in combination. Furthermore, the characteristics such as auxotrophy, analog-resistance, and metabolic regulation mutation can be imparted in combination with enhancement of the biosynthetic enzyme(s).

An auxotrophic mutant strain, an L-amino acid analog-resistant strain or a metabolic regulation mutant strain, which have an ability to produce an L-amino acid, can be obtained by subjecting a parent strain or wild-type strain to a conventional mutation treatment, namely X-ray or UV irradiation, or to a treatment with a mutagen such as N-methyl-N-nitro-N-nitrosoguanidine (NTG) or ethyl methanesulfonate (EMS), and then selecting those which exhibit autotrophy, analog resistance, or a metabolic regulation mutation and have the ability to produce a desired L-amino acid.

L-amino acid-producing bacteria or methods of construction thereof will now be described.

L-Glutamic Acid-Producing Bacteria

Examples of parent strains which can be used to derive L-glutamic acid-producing bacteria include, but are not limited to, strains belonging to the genus *Escherichia* such as *E. coli* VL334thrC+ (VKPM B-8961: EP 1172433). *E. coli* VL334 (VKPM B-1641) is an L-isoleucine and L-threonine auxotrophic strain with mutations in the thrC and ilvA genes (U.S. Pat. No. 4,278,765). A wild-type allele of the thrC gene was introduced to this strain by an ordinary transduction method using a bacteriophage P1 grown on the cells of wild-type *E. coli* K12 strain (VKPM B-7), and as a result, an L-isoleucine auxotrophic L-glutamic acid-producing bacterium VL334thrC+ was obtained.

Examples of methods of modifying a bacterium to impart an ability to produce L-glutamic acid or to enhance the ability to produce L-glutamic acid include modifying a bacterium so that the expression of a gene which encodes an enzyme involved in L-glutamic acid biosynthesis is enhanced. Examples of the enzyme involved in L-glutamic acid biosynthesis include glutamate dehydrogenase (hereinafter, also referred to as "GDH") (gdhA), glutamine synthetase (glnA), glutamate synthetase (gltAB), isocitrate dehydrogenase (icdA), aconitate hydratase (acnA, acnB), citrate synthase (hereinafter, also referred to as "CS") (gltA), methylcitrate synthase (hereinafter, also referred to as "PRPC") (prpC), phosphoenolpyruvate carboxylase (hereinafter, also referred to as "PEPC") (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), and glucose phosphate isomerase (pgi). Here, the abbreviations in parentheses after each enzyme name are the gene names encoding the respective enzyme (the same applies throughout this specification). Among these enzymes, CS, or one or more of PRPC, PEPC, and GDH are particular examples (see WO2006/051660).

Methods of modifying a bacterium so that the expression of a target gene is enhanced will now be described.

The first method is to increase the copy number of a target gene. For instance, the copy number of the gene can be increased by cloning the target gene on an appropriate plasmid and transforming a host bacterium using the obtained plasmid. For example, when one of the genes encoding CS (gltA gene), PRPC (prpC gene), PEPC (ppc gene), or GDH (gdhA gene) is used as the target gene, since the nucleotide sequences of these genes in *Escherichia* bacteria and *Corynebacterium* bacteria have already been determined (Biochemistry, vol. 22, p. 5243-5249, 1983; J. Biochem., vol. 95, p. 909-916, 1984; Gene, vol. 27, p. 193-199, 1984; Microbiology, vol. 140, p. 1817-1828, 1994; Mol. Gen. Genet., vol. 218, p. 330-339, 1989; and Molecular Microbiology, vol. 6, p. 317-326, 1992), these genes can be obtained by synthesizing primers based on the respective nucleotide sequences and carrying out PCR using chromosomal DNA of a bacterium belonging to the Enterobacteriaceae family as the template.

Examples of the plasmid which can be used for transformation include plasmids capable of autonomously replicating in a bacterium belonging to the Enterobacteriaceae family, such as pUC19, pUC18, pBR322, RSF1010, pHSG299, pHSG298, pHSG399, pHSG398, pSTV28, pSTV29 (pHSGs and pSTVs are available from Takara Bio Inc.), pMW119, pMW118, pMW219, and pMW218 (pMWs are available from Nippon Gene Co., Ltd.). Instead of a plasmid, a phage DNA may be used as a vector. Examples of a plasmid which can be used to simultaneously enhance the activities of the aforementioned CS, PRPC, PEPC, and/or GDH include RSFCPG, in which the gltA, ppc, and gdhA genes are incorporated (see EP 0952221A), and RSFPPG, in which the gltA gene of RSFCPG is substituted with the prpC gene (see WO 2008/020654).

Examples of a transformation method include the method reported for *Escherichia coli* K-12 (Mandel, M. and Higa, A. J. Mol. Biol. 53: 159 (1970)) in which recipient bacterial cells are treated with calcium chloride to increase the permeability of DNA, and a method reported for *Bacillus subtilis* (Duncan, C. H., Wilson, G. A. and Young, F. E. Gene 1: 153 (1977)) in which competent cells are prepared from cells at the growth phase, followed by introduction of the DNA.

Alternatively, a known method for *Bacillus subtilis*, actinomycetes, and yeast in which DNA recipient bacterial cells are made into protoplasts or spheroplasts capable of easily taking up recombinant DNA, followed by introduction of the recombinant DNA into the DNA recipient bacterial cells (Chang, S. and Choen, S. N., Molec. Gen. Genet., 168, 111 (1979); Bibb, M J., Ward, J. M. and Hopwood, O. A., Nature, 274, 398 (1978); and Hinnen, A., Hicks, J. B. and Fink, G. R., Proc. Natl. Acad. Sci. USA, 75, 1929 (1978)) may also be employed. In addition, bacterial transformation can also be carried out by an electric pulse method (Japanese Laid-Open Patent Publication No. 2-207791).

The copy number of a gene can also be increased by introducing multiple copies of the target gene onto a bacterial chromosomal DNA. Such introduction of multiple copies of a gene onto a bacterial chromosomal DNA may be carried out by a homologous recombination method in which a sequence present in multiple copies on the chromosomal DNA is used as a target (Experiments in Molecular Genetics, Cold Spring Harbor Lab. (1972)). As the sequence present in multiple copies on the chromosomal DNA, a repetitive DNA and inverted repeat present at the end of a transposon can be used.

Alternatively, as disclosed in Japanese Laid-Open Patent Publication No. 2-109985, it is also possible to introduce multiple copies of a target gene onto chromosomal DNA by introducing the target gene to a transposon and transferring it. Furthermore, a target gene can also be incorporated into a host chromosome by a method using Mu phage (Japanese Laid-Open Patent Publication No. 2-109985).

The second method is to enhance the expression of a target gene on the chromosomal DNA or a plasmid by substituting an expression regulatory sequence of the target gene, such as a promoter, with a stronger one. For example, the lac promoter, tip promoter, trc promoter, PR promoter, lacUV promoter, and the like are known as strong promoters. In addition, as disclosed in WO 00/18935, it is possible to substitute several nucleotides in the promoter region of a gene so that the promoter is stronger. Methods of evaluating the promoter strength and examples of strong promoters are described in the article of Goldstein et al. (Prokaryotic promoters in biotechnology. Biotechnol. Annu. Rev., 1995, 1, 105-128), and the like.

Substitution of an expression regulatory sequence may be carried out, for example, in the same manner as gene substitution using a temperature-sensitive plasmid. Examples of a vector which can be used that has a temperature-sensitive replication origin include the plasmid pMAN997 described in WO 99/03988.

In addition, it is known that a substitution of several nucleotides in the spacer region between the ribosome binding site (RBS) and the start codon, particularly in the sequence immediately upstream of the start codon, significantly affects the translation efficiency of mRNA, and by modifying this sequence, the amount of translation can be improved.

Modification of an expression regulatory sequence can be carried out in combination with the aforementioned method of increasing the copy number of a gene.

Examples of the aforementioned method of gene substitution include methods using a linear DNA, such as a method called "Red-driven integration" (Datsenko, K. A, and Wanner, B. L. Proc. Natl. Acad. Sci. USA. 97: 6640-6645 (2000)) and a method in which the Red-driven integration method and an excision system originated from λ phage (Cho, E. H., Gumport, R. I., Gardner, J. F. J. Bacteriol. 184: 5200-5203 (2002)) are combined (see WO 2005/010175); methods in which a plasmid containing a temperature-sensitive replication origin or a plasmid capable of conjugal transfer is used; and methods utilizing a suicide vector which does not have a replication origin in a host (U.S. Pat. No. 6,303,383 and Japanese Laid-Open Patent Publication No. 05-007491).

For the Red-driven integration, a strain resistant to a λRed gene product, for example, *Pantoea ananatis* SC 17 (0) strain, may be suitably used. This strain has been deposited at the Russian National Collection of Industrial Microorganisms (VKPM), GNII Genetika (address: Russia, 117545 Moscow, 1 Dorozhny proezd. 1) on Sep. 21, 2005, under the deposit number VKPM B-9246.

Examples of bacteria modified by the aforementioned method so that the expression(s) of the citrate synthase gene, methylcitrate synthase gene, phosphoenolpyruvate carboxylase gene, and/or glutamate dehydrogenase gene is/are enhanced include those bacteria described in Japanese Laid-Open Patent Publication Nos. 2001-333769, 2000-106869, 2000-189169, 2000-333769, 2006-129840, WO 2006/051660, and the like.

Furthermore, an ability to produce L-glutamic acid can also be imparted by enhancing the 6-phosphogluconate dehydratase activity or the 2-keto-3-deoxy-6-phosphogluconate aldolase activity, or both of these activities. Examples of bacteria having an increased 6-phosphogluconate dehydratase activity and/or 2-keto-3-deoxy-6-phosphogluconate aldolase activity include the bacterium disclosed in Japanese Laid-Open Patent Publication No. 2003-274988.

The modification for imparting or enhancing an ability to produce L-glutamic acid can also be carried out by reducing or eliminating the activity of an enzyme which catalyzes a reaction which branches off from the L-glutamic acid biosynthetic pathway and produces another compound. Examples of an enzyme which catalyzes a reaction which branches off from the L-glutamic acid biosynthesis pathway and produces a compound other than L-glutamic acid include 2-oxoglutarate dehydrogenase (α-ketoglutarate dehydrogenase) (sucA), isocitrate lyase (aceA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and 1-pyrroline-5-cathoxylate dehydrogenase (putA). Among these, a particular example is to reduce or eliminate the activity of 2-oxoglutarate dehydrogenase.

In order to reduce or eliminate the activities of the aforementioned enzymes, a mutation which reduces or eliminates intracellular activities of the enzymes may be introduced into the genes of the aforementioned enzymes by a conventional mutagenesis method or a genetic engineering technique. Examples of the mutagenesis method include a method using X-ray or UV irradiation, and a treatment method using N-methyl-N-nitro-N-nitrosoguanidine or the like. The gene site to which such mutation is introduced may be a coding region which encodes an enzyme protein or an expression regulatory region such as a promoter or the like. Furthermore, examples of the genetic engineering technique include using genetic recombination, transduction, cell fusion and/or the like.

A decrease or deficiency in the intracellular activity of a target enzyme and the degree of the decrease in the activity can be verified by measuring the enzyme activity of a cell extract or a purified fraction of a candidate strain and comparing it with that of a wild-type strain. For example, the activity of 2-oxoglutarate dehydrogenase can be measured in accordance with the method of Reed et al. (L. J. Reed and B. B. Mukherjee, Methods in Enzymology 1969, 13, p. 55-61).

Examples of bacteria belonging to the genus *Escherichia* having a deficiency in the 2-oxoglutarate dehydrogenase activity or a decreased 2-oxoglutarate dehydrogenase activity include the following strains (U.S. Pat. Nos. 5,378,616 and 5,573,945).

*Escherichia coli* W3110sucA::Kmr
*Escherichia coli* AJ12624 (FERM BP-3853)
*Escherichia coli* AJ12628 (FERM BP-3854)
*Escherichia coli* AJ12949 (FERM BP-4881)

The *Escherichia coli* W3110sucA::Kmr is obtained by disrupting the 2-oxoglutarate dehydrogenase gene (sucA gene) of *Escherichia coli* W3110. This strain is completely deficient in 2-oxoglutarate dehydrogenase.

As the 2-oxoglutarate dehydrogenase gene, the sucA gene of *Escherichia coli* having the nucleotide sequence shown in SEQ ID NO: 9 is exemplified; however, it may also be a homolog gene having a homology of not less than 70%, not less than 80%, not less than 90%, or not less than 95% to SEQ ID NO: 9.

Specific examples of other bacteria having a deficiency or decrease in the 2-oxoglutarate dehydrogenase activity include the following strains.

*Pantoea ananatis* AJ13601 (FERM BP-7207, EP1078989A)

*Pantoea ananatis* AJ13356 (FERM BP-6615, U.S. Pat. No. 6,331,419)

*Pantoea ananatis* SC17sucA (FERM BP-8646, WO 2005/085419)

*Klebsiella planticola* AJ13410 (FERM BP-6617, U.S. Pat. No. 6,197,559)

The SC17sucA strain is obtained by selecting a low phlegm-producing mutant strain (SC17) from AJ13355 strain, which was isolated from nature as a strain capable of proliferating in a medium containing L-glutamic acid and a carbon source at a low pH, and then disrupting the 2-oxoglutarate dehydrogenase gene (sucA) of the mutant strain. The AJ13601 is obtained by introducing the plasmid RSFCPG containing the gltA, ppc, and gdhA genes originating from, and native to, *Escherichia coli* and the plasmid pSTVCB containing the gltA gene originating from, and native to, *Brevibacterium lactofermentum*, into the aforementioned SC17sucA strain to obtain the SC17sucA/RSFCPG+pSTVCB strain, and then further selecting therefrom a high-concentration of a L-glutamic acid resistant strain at a low pH, and selecting a strain having a high proliferation level and a high L-glutamic acid-producing ability (EP 0952221A). The AJ13356 is obtained by making the αKGDH-E1 subunit gene (sucA) deficient in the AJ13355 strain.

The AJ13355 and AJ13356 were deposited at the National Institute of Bioscience and Human Technology (currently, International Patent Organism Depositary, National Institute of Advanced Industrial Science and Technology; address: AIST Tsukuba Central 6, 1-1-1 Higashi, Tsukuba, Ibaraki 305-8566, Japan) on Feb. 19, 1998, under the deposit numbers PERM P-16644 and FERM P-16645, respectively, and converted to international deposit under the provisions of the Budapest Treaty on Jan. 11, 1999, under the deposit numbers PERM BP-6614 and FERM BP-6615, respectively. The SC17sucA strain, which was assigned private number AJ417, was deposited at the International Patent Organism Depositary, National Institute of Advanced Industrial Science and Technology (address: AIST Tsukuba Central 6, 1-1-1 Higashi, Tsukuba, Ibaraki 305-8566, Japan) on Feb. 26, 2004, under the deposit number FERM BP-08646. The AJ13601 strain has been deposited at the National Institute of Bioscience and Human Technology (currently, International Patent Organism Depositary, National Institute of Advanced Industrial Science and Technology; address: AIST Tsukuba Central 6, 1-1-1 Higashi, Tsukuba, Ibaraki 305-8566, Japan) on Aug. 18, 1999, under the deposit number PERM P-17516, and converted to international deposit under the provisions of the Budapest Treaty on Jul. 6, 2000, under the deposit number FIRM BP-7207.

The aforementioned *Pantoea ananatis* AJ13355, AJ13356, and AJ13601 strains, and the *Klebsiella planticola* AJ13399 strain, when cultured under acidic conditions, have an ability to produce L-glutamic acid in an amount exceeding the saturation concentration in a liquid medium.

Furthermore, in order to improve the L-glutamic acid-producing ability of a bacterium belonging to the Enterobacteriaceae family, the arcA gene (U.S. Pat. No. 7,090,998) can be deleted, and a glutamic acid secretion gene, such as the yhfK gene (WO 2005/085419) can be amplified. In addition, a method using the yggB gene (Japanese Laid-Open Patent Publication No. 2007-097573) can also be used.

The aforementioned methods of enhancing or deleting an enzyme activity are also applicable in the same manner to bacteria producing other amino acids described below.

L-Arginine-Producing Bacteria

Examples of a parent strain which can be used to derive an L-arginine-producing bacterium include, but are not limited to, strains belonging to the genus *Escherichia* such as *E. coli* strain 237 (VKPM B-7925) (U.S. Patent Application No. 2002/058315A1) and its derivative strains harboring a mutant N-acetylglutamate synthetase (Russian Patent Application No. 2001112869); *E. coli* strain 382 (VKPM B-7926) (EP 1170358 A1); and an arginine-producing strain into which the argA gene encoding N-acetylglutamate synthetase is introduced (EP 1170361 A1).

Examples of a parent strain which can be used to derive an L-arginine-producing bacterium also include strains in which expression(s) of one or more genes encoding an enzyme of the L-arginine biosynthetic pathway is/are enhanced. Examples of such genes include N-acetylglutamyl phosphate reductase gene (argC), ornithine acetyl transferase gene (argJ), N-acetylglutamate kinase gene (argB), acetylornithine transaminase gene (argD), ornithine cathamoyl transferase gene (argF), argininosuccinic acid synthetase gene (argG), argininosuccinic acid lyase gene (argH), and cathamoyl phosphate synthetase gene (carAB).

L-Threonine-Producing Bacteria

Examples of a parent strain which can be used to derive an L-threonine-producing bacterium include, but are not limited to, strains belonging to the genus *Escherichia* such as *E. coli* TDH-6/pVIC40 (VKPM B-3996) (U.S. Pat. Nos. 5,175,107 and 5,705,371); *E. coli* 472T23/pYN7 (ATCC 98081) (U.S. Pat. No. 5,631,157); *E. coli* NRRL-21593 (U.S. Pat. No. 5,939,307); *E. coli* FERM BP-3756 (U.S. Pat. No. 5,474,918); *E. coli* FERM BP-3519 and FERM BP-3520 (U.S. Pat. No. 5,376,538); *E. coli* MG442 (Gusyatiner et al., Genetika (in Russian), 14, 947-956 (1978)); and *E. coli* VL643 and *E. coli* VL2055 (EP 1149911 A).

The TDH-6 strain is deficient in the thrC gene and sucrose-assimilative, and its ilvA gene has a leaky mutation. This strain also has a mutation in the rhtA gene which imparts resistance to a high concentration of threonine or homoserine. The VKPM B-3996 strain carries the plasmid pVIC40 obtained by inserting thrA*BC operon containing a mutant thrA gene into a RSF1010-derived vector. This mutant thrA gene encodes aspartokinase-homoserine dehydrogenase I substantially desensitized to feedback inhibition by threonine. The VKPM B-3996 strain was deposited at the All-Union Scientific Center of Antibiotics (Nagatinskaya Street 3-A, 117105 Moscow, Russia) on Nov. 19, 1987, under the deposit number RIA 1867. This strain was also deposited at the Russian National Collection of Industrial Microorganisms (VKPM) (1 Dorozhny proezd., 1 Moscow 117545, Russia) on Apr. 7, 1987, under the deposit number VKPM B-3996.

The *E. coli* VKPM B-5318 (EP 0593792 B) can also be used as a parent strain to derive the L-threonine-producing bacterium. The B-5318 strain is an isoleucine non-auxotrophic strain, and the regulatory region of threonine operon in the plasmid pVIC40 is replaced by the temperature-sensitive lambda-phage C1 repressor and PR promoter. The VKPM B-5318 was deposited at the Russian National Collection of Industrial Microorganisms (VKPM) (address: Russia, 117545 Moscow, 1 Dorozhny proezd. 1) on May 3, 1990, under the deposit number VKPM B-5318.

The L-threonine-producing bacterium can be further modified so that expression(s) of one or more of the genes listed below is/are enhanced:

a mutant thrA gene which encodes aspartokinase-homoserine dehydrogenase I resistant to feedback inhibition by threonine;

the thrB gene encoding homoserine kinase;

the thrC gene encoding threonine synthase;

the rhtA gene encoding a putative transmembrane protein;

the asd gene encoding aspartate-β-semialdehyde dehydrogenase; and the aspC gene encoding aspartate aminotransferase (aspartate transaminase).

The thrA gene of *E. coli* which encodes aspartokinase-homoserine dehydrogenase I has been sequenced (nucleotide numbers 337 to 2799, GenBank accession NC_000913.2, gi: 49175990). The thrA gene is located between the thrL and thrB genes on the chromosome of *E. coli* K-12. The thrB gene of *E. coli* which encodes homoserine kinase has been sequenced (nucleotide numbers 2801 to 3733, GenBank accession NC_000913.2, gi: 49175990). The thrB gene is located between the thrA and thrC genes on the chromosome of *E. coli* K-12. The thrC gene of *E. coli* which encodes threonine synthase has been sequenced (nucleotide numbers 3734 to 5020, GenBank accession NC_000913.2, gi: 49175990). The thrC gene is located between the thrB gene and the yaaX open reading frame on the chromosome of *E. coli* K-12. All of these three genes function as a single threonine operon. In order to enhance the expression of the threonine operon, the attenuator region which affects transcription can be removed from the operon (WO2005/049808 and WO2003/097839).

The mutant thrA gene which encodes aspartokinase-homoserine dehydrogenase I resistant to feedback inhibition by threonine, as well as the thrB and thrC genes, can be obtained as one operon from the well-known plasmid pVIC40, which is present in the threonine-producing *E. coli* strain VKPM B-3996. The plasmid pVIC40 is described in detail in U.S. Pat. No. 5,705,371.

The rhtA gene exists at 18 min on the *E. coli* chromosome close to the glnHPQ operon which encodes components of the glutamine transport system. The AAA gene is identical to ORF1 (ybiF gene, nucleotide numbers 764 to 1651, GenBank accession No. AAA218541, gi: 440181) and is located between the pexB and ompX genes. The unit expressing a protein encoded by the ORF1 is called the rhtA gene (rht: resistance to homoserine and threonine). In addition, it has been revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif., Aug. 24-29, 1997, abstract No. 457, EP 1013765 A).

The asd gene of *E. coli* has already been sequenced (nucleotide numbers 3572511 to 3571408, GenBank accession NC_000913.1, gi: 16131307), and can be obtained by PCR using primers prepared based on the nucleotide sequence of the gene (see White, T. J. et al., Trends Genet, 5, 185 (1989)). The asd genes of other microorganisms can be obtained in the same manner.

Furthermore, the aspC gene of *E. coli* has also already been sequenced (nucleotide numbers 983742 to 984932, GenBank accession NC_000913.1, gi: 16128895), and can be obtained by PCR. The aspC genes of other microorganisms can be obtained in the same manner.

<1-2> Attenuation of YdcI Activity

The bacterium can have an ability to produce an L-amino acid, such as L-glutamic acid, L-arginine, and L-threonine, and can be modified so that the activity of a protein encoded by the ydcI gene is attenuated. The ability to produce an L-amino acid such as L-glutamic acid, L-arginine, and L-threonine can also be imparted after modifying the bacterium so that the activity of a protein encoded by the ydcI gene is attenuated.

As described above, the protein encoded by the ydcI gene is presumed to be a LysR-type transcription factor and the activity of the protein is presumed to be DNA binding activity. The term "DNA binding activity" can mean an activity of the YdcI protein to bind to a specific DNA sequence.

The DNA binding activity can be measured, for example, in accordance with the method described in Linda Jen-Jacobson, Structural-perturbation approaches to thermodynamics of site-specific protein-DNA interactions, Methods in Enzymology, Volume 259, 1995, p. 305-344.

The phrase "modified so that the activity of a protein encoded by the ydcI gene is attenuated" can mean, for example, when the expression of the ydcI gene per cell is reduced with respect to a non-modified strain such as a wild-type strain or the parent strain. When the expression of the ydcI gene is reduced can also mean that the translation of the YdcI protein is reduced.

Examples of a non-modified strain which can act as a control, such as a wild-type strain belonging to the Enterobacteriaceae family, include *Escherichia coli* MG1655 strain (ATCC No. 47076), *Escherichia coli* W3110 strain (ATCC No. 27325) and *Pantoea ananatis* AJ13335 strain (FERM BP-6615).

A decrease in the expression of the ydcI gene of a modified strain in comparison with a non-modified strain such as the parent strain or wild-type strain can be verified by comparing the mRNA amount of the modified strain with that of a wild-type or non-modified strain. Examples of the method of verifying the expression amount include Northern hybridization and RT-PCR (Molecular cloning (Cold spring Harbor Laboratory Press, Cold spring Harbor (USA), 2001)). The expression may be reduced by any amount in comparison with a non-modified strain; however, the expression can be reduced not more than ½-fold, more than ⅓-fold, or not more than ⅕-fold, as compared to, for example, a non-modified strain. In addition, a decrease in the expression of the ydcI gene can also be verified by a decrease in the amount of protein encoded by the ydcI gene in comparison with a non-modified strain, and for example, such a decrease in the expression can be detected by Western blotting using an antibody (Molecular cloning (Cold spring Harbor Laboratory Press, Cold spring Harbor (USA), 2001)).

The ydcI gene which is present on the chromosome of the chosen bacteria can be used, and examples thereof include the ydcI gene of *Escherichia coli* (SEQ ID NO: 1: GenBank Accession No. A64894 [GI: 7466846]) which encodes a protein having the amino acid sequence shown in SEQ ID NO: 2, and its homolog genes. Furthermore, examples of the ydcI gene also include the ydcI gene of *Pantoea ananatis* which encodes a protein having the amino acid sequence shown in SEQ ID NO: 12 or 14, and homolog genes thereof.

The term "ydcI homolog gene" can refer to a gene which originates from, or is native to, another microorganism, has a structure highly similar to that of the ydcI genes of *Escherichia* and *Pantoea* bacteria, and improves, when the expression thereof is reduced, the ability to produce L-glutamic acid or L-arginine in a host. The gene can encode a protein exhibiting DNA binding activity. Examples of the ydcI homolog include genes from bacteria belonging to the genera *Shigella*, *Enterobacter*, and the like, which genes have been registered at GenBank. Furthermore, the ydcI gene may also be cloned based on the homology with the aforementioned genes from a bacterium belonging to the genus *Streptomyces* such as *Streptomyces coelicolor* or a lactic acid bacterium such as one belonging to the genus *Lactococcus* or *Lactobacillus*. When the ydcI gene has a high homology with that of a bacterium belonging to the genus *Escherichia* or *Pantoea*, a different gene name may also be assigned to the ydcI gene.

In addition, ydcI gene homologs that have a high homology can be obtained from a known database based on the aforementioned sequence information. The homology of an amino acid sequence and nucleotide sequence can be determined by using, for example, algorithm BLAST (Proc. Natl. Acad. Sci. USA, 90, 5873 (1993)) or FASTA (Methods Enzymol., 183, 63 (1990)). Based on this algorithm BLAST, programs called BLASTN and BLASTX have been developed (see www.ncbi.nlm.nih.gov).

Furthermore, the ydcI gene is not restricted to a wild-type gene, and as long as the functions of the encoded protein, namely DNA binding activity, are not impaired, the ydcI gene can also encode a protein having the amino acid sequence shown in SEQ ID NO: 2, 12 or 14, except that one or several amino acids are substituted, deleted, inserted, added or the like at one or more positions.

The term "one or several" or "one or more", although it can vary depending on the position(s) of the amino acid residue(s) in the spatial structure of the protein and the type thereof, can refer to 1 to 20, 1 to 10, or 1 to 5. The aforementioned one or several substitutions, deletions, insertions or additions of amino acids can be conservative mutations that retain DNA binding activity. The term "conservative mutation" can refer to a mutation of mutual substitution among Phe, Trp and Tyr in the case of aromatic amino acids; among Leu, Be and Val in the case of hydrophobic amino acids; between Gln and Asn in the case of polar amino acids; among Lys, Arg and His in the case of basic amino acids; between Asp and Glu in the case of acidic amino acids; and between Ser and Thr in the case of amino acids having a hydroxyl group. Representative examples of the conservative mutation include conservative substitutions, and specific examples of mutation regarded as the conservative substitution include a substitution of Ala with Ser or Thr; a substitution of Arg with Gln, His or Lys; a substitution of Asn with Glu, Gln, Lys, His or Asp; a substitution of Asp with Asn, Glu or Gln; a substitution of Cys with Ser or Ala; a substitution of Gln with Asn, Glu, Lys, His, Asp or Arg; a substitution of Glu with Gly, Asn, Gln, Lys or Asp; a substitution of Gly with Pro; a substitution of His with Asn, Lys, Gln, Arg or Tyr; a substitution of Be with Leu, Met, Val or Phe; a substitution of Leu with Be, Met, Val or Phe; a substitution of Lys with Asn, Glu, Gln, His or Arg; a substitution of Met with Be, Leu, Val or Phe; a substitution of Phe with Tip, Tyr, Met, Be or Leu; a substitution of Ser with Thr or Ala; a substitution of Thr with Ser or Ala; a substitution of Trp with Phe or Tyr; a substitution of Tyr with His, Phe or Trp; and a substitution of Val with Met, Be or Leu. Furthermore, the aforementioned amino acid substitution, deletion, insertion, addition, inversion and the like also encompass those caused by a naturally-occurring mutation (mutant or variant) based on, for example, individual difference or species difference of microorganisms retaining the ydcI gene.

Furthermore, as the ydcI gene, a sequence which encodes a protein having a homology of not less than 80%, not less than 90%, not less than 90%, or not less than 97% to the whole amino acid sequence shown in SEQ ID NO: 2, 12 or 14, and has DNA binding activity may also be used.

The ydcI gene can also be DNA which hybridizes, under stringent conditions, with the complementary sequence of the nucleotide sequence shown in 301-1221 of SEQ ID NO: 1, 301-1230 of SEQ ID NO: 11 or 301-1218 of SEQ ID NO: 13 or with a probe which can be prepared from these sequences, and encodes a protein having DNA binding activity. The term "stringent conditions" can refer to conditions in which a so-called specific hybrid is formed and non-specific hybrid is not formed. It is difficult to clearly represent these conditions in numerical values; however, examples of the stringent conditions include conditions in which DNAs having a high homology to each other, for example, DNAs having a homology of not less than 80%, not less than 90%, not less than 95%, or not less than 97% hybridize with each other and DNAs having a lower homology do not hybridize with each other; and conditions in which washing is carried out once, or 2 to 3 times at a salt concentration and temperature corresponding to ordinary washing conditions of Southern hybridization, 60° C., 1×SSC, 0.1% SDS, 0.1×SSC, 0.1% SDS, or 68° C., 0.1×SSC, 0.1% SDS.

As the probe, a part of the complementary sequence of 301-1221 of SEQ ID NO: 1, 301-1230 of SEQ ID NO: 11 or 301-1218 of SEQ ID NO: 13 can also be used. Such a probe can be prepared by PCR in which oligonucleotides prepared based on the complementary sequence of 301-1221 of SEQ ID NO: 1, 301-1230 of SEQ ID NO: 11 or 301-1218 of SEQ ID NO: 13 are used as primers and a DNA fragment containing these nucleotide sequences is used as the template. When a DNA fragment having a length of approximately 300 bps is used as the probe, examples of the washing conditions after hybridization include 50° C., 2×SSC, 0.1% SDS.

A bacterium having an attenuated activity of a protein encoded by the ydcI gene can be obtained, for example, by substituting the ydcI gene on the chromosome with a ydcI gene which does not normally function (hereinafter, may be referred to as "disrupted-type ydcI gene") by homologous recombination method using gene recombination (Experiments in Molecular Genetics, Cold Spring Harbor Laboratory press (1972); Matsuyama, S. and Mizushima, S., J. Bacteriol., 162, 1196 (1985)).

The mechanism of the homologous recombination is as follows. When a plasmid or the like which has a sequence homologous with a sequence on the chromosome is introduced into a bacterial cell, recombination occurs at the homologous sequence at a certain frequency, thereby the introduced plasmid is entirely incorporated onto the chromosome. Subsequently, when recombination further occurs at the homologous sequence on the chromosome, the plasmid once again is removed from the chromosome; however, depending on the position of the recombination at this time, the disrupted gene can be fixed on the chromosome and the original normal gene can be removed from the chromosome along with the plasmid. By selecting such a strain, a strain in which the normal ydcI gene on the chromosome is replaced by the disrupted-type ydcI gene can be obtained.

Gene disruption technique by homologous recombination has already been established, and for example, a method using a linear DNA and a method using a temperature-sensitive plasmid can be employed. In addition, the ydcI gene can also be disrupted by using a plasmid which cannot be replicated in a bacterial cell of interest and contains the ydcI gene into which a marker gene such as a drug-resistance gene is inserted. That is, a marker gene is incorporated into the chromosomal DNA of a transformant which has been transformed with the aforementioned plasmid and acquired drug resistance. This marker gene is highly likely to be incorporated by homologous recombination between the ydcI gene sequences on both ends thereof and these sequences on the chromosome; therefore, the gene-disrupted strain can be efficiently selected.

Examples of a temperature-sensitive plasmid which functions in a bacterium belonging to the genus *Escherichia* include pMAN997 (WO 99/03988), as well as pHSG415 and pHSG422 (Hashimoto-Gotoh, T. et al., Gene, 16, 227-235 (1981)).

Specifically, the disrupted-type ydcI gene used in the gene disruption can be obtained by carrying out, for example, deletion of a certain region of the gene by restriction enzyme digestion and re-ligation, insertion of another DNA fragment (such as marker gene) into the gene, site-specific mutagenesis (Kramer, W. and Frits, H. J., Methods in Enzymology, 154, 350 (1987)), or treating with a chemical agent such as sodium hyposulfite or hydroxylamine (Shortle, D. and Nathans, D., Proc. Natl. Acad. Sci. U.S.A., 75, 270 (1978)), so as to allow one or more nucleotide substitutions, deletions, insertions, additions or inversions to occur in the nucleotide sequence(s) of the ydcI gene coding region, promoter region and/or the like, thereby reducing or eliminating the activity of the encoded protein or the transcription of the ydcI gene. Among these embodiments, from the standpoints of the reliability and safety, a method of deleting a certain region of the ydcI gene by restriction enzyme digestion and re-ligation or a method of inserting other DNA fragment into the gene can be used.

Disruption of the ydcI gene can be verified by analyzing the gene on the chromosome by Southern blotting or PCR.

Methods of obtaining various genes, hybridization, PCR, preparation of a plasmid DNA, DNA cleavage and ligation, transformation and the like are described in Sambrook, J., Fritsch, E. F., Maniatis, T., Molecular Cloning, Cold Spring Harbor Laboratory Press, 1.21 (1989)).

In addition, a mutant strain not capable of producing functional ydcI protein can also be obtained by treating a γ-proteobacterium with UV irradiation or a mutagen used in a conventional mutagenesis treatment, such as N-methyl-N-nitrosoguanidine (NTG) or nitrous acid.

<2> Method of Producing L-Amino Acid Such as L-Glutamic Acid, L-Arginine and L-Threonine An L-amino acid such as L-glutamic acid, L-arginine, and L-threonine can be produced by culturing in a medium the bacterium obtained in the aforementioned manner, which has an ability to produce an L-amino acid such as L-glutamic acid, L-arginine, and L-threonine, and is modified so that the intracellular activity of the ydcI protein is attenuated, to allow a desired substance to be produced and accumulated in the medium or in the bacterial cells, and then collecting the L-amino acid.

As the medium used in the culturing, an ordinary medium which contains a carbon source, nitrogen source, inorganic salts and, as required, organic trace nutrients such as amino acids and vitamins, can be employed. The medium can also be either a synthetic or natural medium. The carbon source and nitrogen source can be any kind as long as they can be utilized by the strain to be cultured.

As the carbon source, sugars such as glucose, glycerol, fructose, sucrose, maltose, mannose, galactose, starch hydrolysates and molasses can be used. In addition, organic acids such as acetic acid and citric acid and alcohols such as ethanol can also be used individually or in combination with other carbon source(s). As the nitrogen source, ammonia, ammonium salts such as ammonium sulfate, ammonium carbonate, ammonium chloride, ammonium phosphate and ammonium acetate, nitrate salts, and the like can be used. As the organic trace nutrient, amino acids, vitamins, fatty acids, and nucleic acids, as well as those substances containing these nutrients, such as peptone, casamino acid, yeast extract, and soybean protein hydrolysate, can be used. In cases where an auxotrophic mutant strain which requires an amino acid or the like for its growth is used, the required nutrient can be supplemented.

Particularly, when a liquid medium is prepared so that precipitation of L-glutamic acid is allowed, L-glutamic acid can be more efficiently crystallized by supplementing the medium with panthothenic acid (WO 2004/111258). As the inorganic salts, phosphates, magnesium salts, calcium salts, iron salts, manganese salts and the like can be used.

The culturing can be carried out under aeration by controlling the fermentation temperature at 20 to 45° C. and pH at 3 to 9. When the pH decreases during the culturing, the medium can be neutralized by, for example, adding calcium carbonate or an alkali such as ammonia gas. The desired amino acid can be accumulated in the culture medium by culturing under such conditions for approximately 10 to 120 hours.

In addition, a liquid medium which is prepared so that precipitation of L-glutamic acid is allowed can also be used for culturing while allowing precipitation of L-glutamic acid in the medium. Such conditions in which L-glutamic acid is precipitated include pH 5.0 to 4.0, pH 4.5 to 4.0, pH 4.3 to 4.0, or pH 4.0.

Furthermore, when allowing L-glutamic acid to precipitate in the medium, more efficient crystallization thereof may be attained by the addition of a crystal of L-glutamic acid or L-lysine as seed crystal in advance (EP 1233069 and EP Patent Application No. 1624069).

After completion of the culturing, the L-amino acid can be collected from the culture medium in accordance with a known collection method. For example, the L-amino acid can be collected by a method in which the culture medium is concentrated and crystallized after removal of bacterial cells or by a method such as ion-exchange chromatography. When the culturing is carried out under conditions which allow L-glutamic acid to precipitate, the L-glutamic acid precipitated in the culture medium may be collected by centrifugation, filtration or the like. In this case, L-glutamic acid dissolving in the medium can be precipitated and then separated together with already precipitated L-glutamic acid.

When producing L-arginine, the production can be performed by a method in which fermentation is carried out by controlling the pH of the medium during culturing to be 6.5 to 9.0 and the pH of the medium after completion of the culturing to be 7.2 to 9.0 and controlling the inner pressure of the fermentation vessel during fermentation to be positive, or by providing carbon dioxide or a mixed gas containing carbon dioxide to the medium, so that there is a period during the culturing in which bicarbonate ions and/or carbonate ions are present in an amount of at least 2 g/L in the medium, which bicarbonate ions and/or carbonate ions serve as counter ions of cations that are primarily basic amino acids (see Japanese Laid-Open Patent Publication No. 2002-065287 and U.S. Patent Application Publication No. 2002025564).

EXAMPLES

The present invention will now be explained more concretely by way of the following non-limiting examples.

Example 1

Production by *Escherichia coli* sucA and ydcI Genes Double-Disrupted Strain

The sucA gene of *Escherichia coli* was deleted using MG1655 ΔsucA described in Japanese Laid-Open Patent Publication No. 2004-89188 (P2004-89188A). Deletion of the ydcI gene was carried out in accordance with a method called "Red-driven integration" originally developed by Datsenko and Wanner (Proc. Natl. Acad. Sci. USA, 2000, vol. 97, No. 12, p 6640-6645). According to this method, a gene-disrupted strain can be constructed in one step by using a PCR product obtained by using a synthetic oligonucleotide sequence having the target gene towards the 5' end and an antibiotic resistance gene towards the 3' end.

The entire nucleotide sequence of the genomic DNA of *Escherichia coli* K-12 strain has already been determined (Blattner F. R., Plunkett G., Bloch C. A. et al., Science, 227, 1453-1474 (1997)). A gene-disrupted strain was prepared based on the known nucleotide sequence of the ydcI gene.

As the template for PCR, plasmid pMW118-attL-Cm-attR was used. The pMW118-attL-Cm-attR is obtained by inserting attachment sites of λ phage, the attL and attR genes, and an antibiotic resistance gene, the cat gene, into pMW118 (manufactured by NIPPON GENE CO., LTD) in the order of attL-cat-attR. The attL and the attR sequences are shown in SEQ ID NO: 3 and SEQ ID NO: 4, respectively.

Complementary primers were designed for each of the regions adjacent to the ydcI gene, and the gene imparting antibiotic resistance to the template plasmid. Two synthetic DNA primers, shown in SEQ ID NOs: 5 and 6, were synthesized by a conventional method. Using these primers and the pMW118-attL-Cm-attR as the template, PCR was performed.

The thus amplified PCR product was purified using QIAGEN PCR Purification Kit (Cat No. 28104), and then used for electroporation of MG1655 ΔsucA containing plasmid pKD46 having a temperature-sensitive replication origin (hereinafter, referred to as MG1655 ΔsucA/pKD46). The plasmid pKD46 (Proc. Natl. Acad. Sci. USA, 2000, vol. 97, No. 12, p 6640-6645) contains a DNA fragment of λ phage having a total of 2,154 nucleotides (GenBank/EMBL accession No. J02459, 31088th to 33241st), and which also contains genes of the λRed system (λ, β and exo genes) that are regulated by arabinose-inducible ParaB promoter. The plasmid pKD46 is necessary for incorporating the PCR product into the MG1655 ΔsucA.

Competent cells for electroporation were prepared in the following manner. In LB medium containing 100 mg/L of ampicillin, the MG1655 ΔsucA/pKD46 was cultured overnight at 30° C. and the resulting culture was diluted 100-fold with 5 mL of LB medium containing ampicillin and L-arabinose (1 mM). The thus obtained dilution was allowed to grow at 30° C. under aeration until OD600 reached approximately 0.6. Subsequently, the resulting solution was washed three times with ice-cold 1 mM HEPES (pH 7.0) in preparation for electroporation. The electroporation was carried out using 50 µL of the thus obtained competent cells and approximately 100 ng of the PCR product. After the electroporation, 1 mL of SOC medium (Molecular Cloning: A Laboratory Manual Second Edition. Sambrook, J. et al., Cold Spring Harbor Laboratory Press (1989)) was added to the cells, and cultured at 37° C. for 1 hour. Thereafter, the cells were plate-cultured at 37° C. on an LB agar medium to select a chloramphenicol-resistant recombinant. Next, in order to cure the plasmid pKD46, the thus selected recombinant was subcultured at 37° C. on an LB agar medium containing chloramphenicol. The thus obtained colonies were subjected to an ampicillin resistance test to obtain an ampicillin-sensitive strain lacking the pKD46. A mutant in which the ydcI gene is deleted could be distinguished by the chloramphenicol resistance gene, and was verified by PCR using the synthetic DNAs shown in SEQ ID NOs: 7 and 8. It was confirmed that the length of the PCR product obtained by using as a template the cellular DNA of the ydcI gene-deficient strain MG1655 ΔsucA,ydcI::cat was longer than that of the wild-type strain. It was also confirmed that the chloramphenicol resistance gene was inserted within the ydcI gene and that, therefore, the ydcI gene was disrupted. The ydcI-disrupted strain in which the chloramphenicol resistance gene was inserted was named the MG1655 ΔsucA ΔydcI strain.

Example 2

Effect of ydcI Deficiency in *Escherichia* L-Glutamic Acid-Producing Strains In order to examine the effect of the ydcI gene disruption on L-glutamic acid fermentation, the MG1655 ΔsucA ΔydcI strain was cultured with the sucA gene-deficient strain MG1655 ΔsucA as control, and the amount of produced L-glutamic acid was measured. The medium, the culturing method and the analytical method used therefor are explained herein.

The MG1655 ΔsucA ΔydcI and the control strain MG1655 ΔsucA were inoculated into LB medium and precultured overnight at 37° C. In a 500 ml-Erlenmeyer flask, ⅙ of the bacterial cells on the plate were inoculated into 50 ml of glucose medium having the composition described below and cultured at 37° C. for 48 hours. After the culturing, L-glutamic acid which had accumulated in the medium was measured by a biotech analyzer (Sakura Seiki Co., Ltd.).

Glucose Medium Composition:

| | |
|---|---|
| Glucose | 40 g/L |
| $MgSO_4 \cdot 7H_2O$ | 1.0 g/L |
| $(NH_4)_2SO_4$ | 20 g/L |
| $KH_2PO_4$ | 1.0 g/L |
| Yeast extract | 2.0 g/L |
| $FeSO_4 \cdot 7H_2O$ | 0.01 g/L |
| $MnSO_4 \cdot 5H_2O$ | 0.01 g/L |
| Thiamine HCl | 0.01 g/L |
| Chloramphenicol | 25 mg/L |
| Calcium carbonate | 30 g/L | pH: 7.0 (adjusted with KOH)
Sterilization conditions: 120° C., 20 minutes

The results are shown in Table 1. Compared to the control MG1655 ΔsucA, the yield of L-glutamic acid (Glu) was largely improved in the MG1655 ΔsucA ΔydcI which contained the disrupted ydcI gene.

Table 1

TABLE 1

Effect of ydcI deficiency in *Escherichia* L-glutamic acid-producing MG1655 ΔsucA strain

| Strain name | OD (600 nm) | Glu concentration (g/l) |
|---|---|---|
| MG1655 ΔsucA | 9.8 | 14.9 |
| MG1655 ΔsucAΔydcI | 10.2 | 16.1 |

Example 3

Confirmation of the Effect of ydcI Deficiency in Arg-Producing *Escherichia coli*

The strain 237 was used as an Arg-producing *Escherichia coli*. The strain 237 was induced from *Escherichia coli* K12 ilvA::Tn5 with 1-methyl-3-nitro-1-nitrosoguanidine, and is a mutant strain which is resistant to the pyrimidine analog 6-azauracil. This strain has been deposited at the Russian National Collection of Industrial Microorganisms (VKPM), GMT Genetika (address: Russia, 117545 Moscow, 1 Dorozhny proezd. 1) under the name of VKPM B-7925. Deletion of the ydcI gene in the strain 237 was carried out in accordance with the method described in Example 1 to obtain the 237ΔydcI strain.

In order to verify the L-arginine yield, the thus obtained 237ΔydcI strain was cultured for evaluation. The culturing was carried out in a test tube under shaking at 37° C. for 50 hours. The composition of the medium was as follows: 60 g/L of glucose, 25 g/L of $(NH_4)_2SO_4$, 5 g/L of yeast extract, 2 g/L of $KH_2PO_4$, 1 g/L of $MgSO_4.7H_2O$, 25 g/L of $CaCO_3$, 0.1 mg/L of Thiamine/HCl and 0.5 g/L of L-threonine. The amount of L-arginine which accumulated in the medium was measured by HPLC. As for the measurement conditions of HPLC, the column INERTSIL ODS-3 manufactured by GL Sciences Inc. (4.0×250 mm) was used, and the buffer which contained, per 1 L thereof, 5.765 g of 85% phosphoric acid and 1.0 g of 98% heptane sodium sulfonate was adjusted to pH 4.5 with sodium hydroxide and then 70 ml of methanol was added to a final volume of 1 L.

Arginine (Arg) was largely improved in 237ΔydcI which contains the disrupted ydcI gene.

Table 2:

TABLE 2

Effect of ydcI deficiency in *Escherichia*
L-arginine-producing 237 strain

| Strain name | OD (600 nm) | Arg concentration (g/l) |
|---|---|---|
| 237 | 13.8 | 2.1 |
| 237 ΔydcI | 13.9 | 2.9 |

Example 4

Preparation of a c1129 Gene-Disrupted Strain and c1705 Gene-Disrupted Strain of *Pantoea ananatis*

The c1129 and c1705 genes of *Pantoea ananatis* encode proteins having amino acid sequences which are not less than 45% identical to the *Escherichia coli* ydcI gene product, and hence were used as ydI gene homologs. The nucleotide sequences of the *Pantoea ananatis* c1129 and c1705 genes are shown in SEQ ID NOs: 11 and 13, respectively, and their amino acid sequences are shown in SEQ ID NOs: 12 and 14, respectively. For preparation of gene-disrupted strains of *Pantoea ananatis*, the SC17 (0) strain was used. This strain was deposited at the Russian National Collection of Industrial Microorganisms (VKPM), GNII Genetika (address: Russia, 117545 Moscow, 1 Dorozhny proezd. 1) on Sep. 21, 2005 under the deposit number VKPM B-9246.

The c1129 and c1705 genes were deleted in accordance with the method described in WO 2008/090770. This method utilizes a method called "Red-driven integration" or "Red-mediated integration" (Proc. Natl. Acad. Sci. USA. 97. 6640-6645 (2000)). According to this method, a gene-disrupted strain can be constructed in one step by using a PCR product obtained by using a synthetic oligonucleotide in which a target gene is designed at the 5' end and an antibiotic resistance gene is designed at the 3' end.

For PCR, the oligonucleotides shown in SEQ ID NOs: 15 and 16 and SEQ ID NOs: 17 and 18 were used as primers, and plasmid pMW118-(λattL-Km$^r$-λattR) was used as the template. As shown in WO 2008/090770, the plasmid pMW118-(λattL-Km$^r$-λattR) is obtained by inserting attachment sites of λ phage, the attL and attR genes, and a kanamycin resistance gene, into pMW118 (manufactured by NIPPON GENE CO., LTD) in the order of attL-Km$^r$-attR.

The amplified PCR product was purified and used for λ-dependent integration into the *Pantoea ananatis* chromosome. Helper plasmid RSF-Red-TER was used as a carrier of the λ phage Red gene. In order to obtain electrocompetent cells of *Pantoea ananatis*, the SC17 (0) strain was transformed with the RSF-Red-Ter plasmid and cultured overnight at 34° C. in an LB medium containing 50 µg/ml of chloramphenicol. Subsequently, the culture medium was diluted 100-fold with a fresh LB medium containing 50 µg/ml of chloramphenicol, and the thus obtained dilution was allowed to grow at 34° C. under aeration until $OD_{600}$ reached 0.3. Thereafter, 1 mM of IPTG was added and culturing was continued until $OD_{600}$ reached 0.7. 10 mM sample was washed three times with an equivalent volume of deionized water and the cells were suspended in 40 µl of 10% cold glycerol. Immediately before electroporation, 100 to 200 ng of in vitro-amplified DNA fragments dissolved in 5 µl of deionized water was added to the cell suspension. Electroporation was carried out by using a bacterial electroporation apparatus ("BioRad", USA, catalog No. 165-2089, Version 2-89).

Immediately after the electroporation, 1 ml of LB medium supplemented with glucose (0.5%) was added to the cell suspension. The cells were allowed to grow at 34° C. for 2 hours under aeration, plated onto an LB solid medium containing 25 µg/ml of chloramphenicol, and incubated overnight at 34° C. The selected Km$^R$ integrant was streaked on an LB medium plate to which IPTG (1 mM) and sucrose (5 g/L) were added and allowed to grow at 34° C. to form single colonies. In order to cure the RSF-Red-TER helper plasmid from the integrant, Km$^R$ and Cm$^S$ variants were isolated. A mutant in which the c1129 gene or the c1705 gene was deleted, and which could be distinguished by the kanamycin resistance gene, was verified by PCR using the synthetic DNAs shown in SEQ ID NOs: 19 and 20 and SEQ ID NOs: 21 and 22. It was confirmed that the length of the PCR products obtained by using the cellular DNAs of the SC17 (0)Δc1129 and SC17 (0)Δc1705 as the template, which are the c1129 gene-disrupted strain and c1705 gene-disrupted strains, respectively, was longer than that of the SC17 (0) strain. It was also confirmed that the kanamycin resistance gene was inserted within the c1129 and c1705 genes and that, therefore, the c1129 and c1705 genes were disrupted. The c1129-disrupted and c1705-disrupted strains in which the kanamycin resistance gene was inserted were named SC17 (0) Δc1129 and SC17 (0) Δc1705 strains, respectively.

Genomic DNAs were extracted from these strains and the NA1 strain (WO 2008/090770) was transformed by electroporation. The NA1 strain was obtained by curing two plasmids, RSFCPG and pSTVCB, from the AJ13601 strain (see Japanese Laid-Open Patent Publication No. 2001-333769) and by introducing a plasmid for L-glutamic acid production, RSFPPG (WO 2008/090770). The AJ13601 strain was deposited at the National Institute of Bioscience and Human Technology, Japanese Ministry of Economy, Trade and Industry (1-1-3 Higashi, Tsukuba, Ibaraki 305-8566, Japan) on Aug. 18, 1999, under the deposit number FERM P-17516 and was converted to an international deposit under the provisions of the Budapest Treaty on Jul. 6, 2000, under the deposit number FERM BP-7207. Furthermore, both of the plasmids RSFCPG and pSTVCB are described in Japanese Laid-Open Patent Publication No. 2001-333769. The RSFCPG is a plasmid containing the gltA, ppc, and gdhA genes originating from, and native to, *Escherichia coli*. The plasmid pSTVCB is obtained by inserting the gltA gene originating from, and native to, *Brevibacterium lactofermentum* into pSTV29 (TakaraBio Inc.).

Minimal medium components (a medium containing 0.5 g of glucose, 2 mM of magnesium sulfate, 3 g of potassium (I) phosphate, 0.5 g of sodium chloride, 1 g of ammonium chloride and 6 g of disodium phosphate in 1 L of pure water), 40 mg/L of kanamycin, 12.5 mg/L of tetracycline hydrochloride and 25 mg/L of chloramphenicol were added to an L medium (a medium containing 10 g of bacto tryptone, 5 g of yeast extract, 5 g of NaCl and 15 g of agar in 1 L of pure water; pH 7.0) on a plate, and NA1 strains into which the genomic DNA from the SC17 (0) Δc1129 or SC17 (0) Δc1705 had been introduced were selected to obtain approximately 20 transformant colonies. These strains had the λattL-Km$^r$-λattR-Ptac fragment inserted into the c1129 gene or the c1709 gene. One clone was selected for each strain, and named NA1 Δc1129 and NA1 Δc1705, respectively.

Example 5

Effect of c1129 Gene Deficiency and c1705 Gene Deficiency in *Pantoea ananatis*

L-Glutamic Acid-Producing Strain

In order to examine the effect of the c1129 and c1705 gene disruption on L-glutamic acid fermentation, the NA1 Δc1129 strain and the NA1 Δc1705 strain were cultured with the NA1 strain as control, and the amount of L-glutamic acid which was produced was measured. The medium, the culturing method, and the analytical method used therefor are explained herein.

The NA1 Δc1129 strain, the NA1 Δc1705 strain, and the control strain NA1 were inoculated into LBGM9 medium and cultured overnight at 34° C. The composition of the LBGM9 medium was as follows: 10 g/L of bacto tryptone, 5 g/L of YE, 10 g/L of NaCl, 40 mg/L of NaOH, 6 g/L of Na$_2$HPO$_4$, 3 g/L of KH$_2$PO$_4$, 0.5 g/L of NaCl, 1 g/L of NH$_4$Cl, 5 g/L of Glc, and 15 g/L of agar. In a 5 ml-test tube, ⅛ of the bacterial cells on the plate were inoculated into a glucose medium having the composition described below and cultured at 37° C. for 24 hours. After the culturing, L-glutamic acid which had accumulated in the medium was measured by a biotech analyzer (Sakura Seiki Co., Ltd.).

Glucose Medium Composition:

| | |
|---|---|
| Glucose | 30 g/L |
| MgSO$_4$·7H$_2$O | 0.5 g/L |
| (NH$_4$)$_2$SO$_4$ | 20 g/L |
| KH$_2$PO$_4$ | 2.0 g/L |
| Yeast extract | 2.0 g/L |
| FeSO$_4$·7H$_2$O | 0.02 g/L |
| MnSO$_4$·5H$_2$O | 0.02 g/L |
| Thiamine HCl | 0.01 g/L |
| Lysine | 0.2 g/L |
| Methionine | 0.2 g/L |
| Diaminopimelic acid | 0.2 g/L |
| Calcium carbonate | 20 g/L | pH: 7.0 (adjusted with KOH)
Sterilization conditions: 115° C., 10 minutes

The results are shown in Table 3. Compared to the control NA1, the yield of L-glutamic acid (Glu) was largely improved in the NA1 Δc1129, which contains the disrupted c1129 gene, and in the NA1 Δc1705, which contains the disrupted c1705 gene.

Table 3:

TABLE 3

Effect of c1129 gene disruption and c1705 disruption in *Pantoea ananatis* L-glutamic acid-producing NA1 strain

| Strain name | OD (600 nm) | Glu concentration (g/l) |
|---|---|---|
| NA1 | 21.9 | 7.1 |
| NA1 Δc1129 | 23.5 | 8.6 |
| NA1 Δc1705 | 22.5 | 9.0 |

Example 6

Effect of ydcI Disruption in *Escherichia* L-Threonine-Producing Strain

*Escherichia coli* VKPM B-5318 strain (see EP 0593792) may be used as an L-threonine-producing strain. This VKPM B-5318 strain (hereinafter, indicated as "B-5318") is an isoleucine non-auxotrophic strain, and retains a recombinant plasmid DNA constructed so that a threonine operon, that is, a gene involved in threonine biosynthesis, whose attenuator region, an intrinsic transcriptional regulatory region, is deleted, is located downstream of the lambda phage's temperature-sensitive C1 repressor, PR promoter, and the N-terminus of Cro protein, thereby the expression of the gene involved in threonine biosynthesis is controlled by the lambda phage repressor and promoter.

Disruption of the ydcI gene in the B-5318 strain is carried out in accordance with the method described in Example 1 to obtain the B-5318 ΔydcI strain.

The B-5318 ΔydcI strain is cultured at 37° C. in an LB medium containing 25 mg/L of kanamycin until OD600 reached approximately 0.6, and an equivalent volume of 40% glycerol solution is added to the culture medium and stirred. Thereafter, the resulting culture is aliquoted in an appropriate amount and stored at −80° C. to obtain a glycerol stock Glycerol stocks of these strains are thawed, and 100 μL of each stock is evenly spread on an L plate containing 25 mg/L of chloramphenicol. These plates are incubated at 37° C. for 24 hours. In a 500 ml-Erlenmeyer Sakaguchi flask, approximately ⅛ of the bacterial cells on the plate are inoculated into 20 mL of fermentation medium described below containing 25 mg/L of chloramphenicol. This is cultured at 40° C. for 18 hours using a reciprocal shaking culture apparatus. After the culturing, the amount of L-threonine which accumulates in the medium is measured by using an amino acid analyzer L-8500 (manufactured by Hitachi Ltd.). The composition of the medium used in the culturing is shown below.

L-threonine Production Medium for *Escherichia* Bacteria:

| | |
|---|---|
| Glucose | 40 g/L |
| (NH$_4$)$_2$SO$_4$ | 16 g/L |
| KH$_2$PO$_4$ | 1.0 g/L |
| MgSO$_4$·7H$_2$O | 1.0 g/L |
| FeSO$_4$·7H$_2$O | 0.01 g/L |
| MnSO$_4$·7H$_2$O | 0.01 g/L |
| Yeast Extract | 2.0 g/L |
| CaCO$_3$ (Japanese Pharmacopoeia) | 30 g/L |

The medium is adjusted to pH 7.0 with KOH and autoclaved at 120° C. for 20 minutes. Glucose and MgSO$_4$.7H$_2$O are mixed and separately sterilized. CaCO$_3$ is dry-heat sterilized before being added.

Compared to the control B-5318, the growth and L-threonine accumulation are increased in the ydcI-deficient strain B-5318ΔydcI.

DESCRIPTION OF SEQUENCE LISTING

SEQ ID NO: 1: Nucleotide sequence of *E. coli* ydcI gene
SEQ ID NO: 2: Amino acid sequence encoded by *E. coli* ydcI gene
SEQ ID NO: 3: Nucleotide sequence of attL
SEQ ID NO: 4: Nucleotide sequence of attR
SEQ ID NO: 5: Nucleotide sequence of 5'-primer for disruption of ydcI
SEQ ID NO: 6: Nucleotide sequence of 3'-primer for disruption of ydcI
SEQ ID NO: 7: Nucleotide sequence of 5'-primer for detection of ydcI disruption
SEQ ID NO: 8: Nucleotide sequence of 3'-primer for detection of ydcI disruption
SEQ ID NO: 9: Nucleotide sequence of *E. coli* sucA gene
SEQ ID NO: 10: Amino acid sequence encoded by *E. coli* sucA gene
SEQ ID NO: 11: Nucleotide sequence of *Pantoea ananatis* c1129 gene
SEQ ID NO: 12: Amino acid sequence encoded by *Pantoea ananatis* c1129 gene
SEQ ID NO: 13: Nucleotide sequence of *Pantoea ananatis* c1705 gene
SEQ ID NO: 14: Amino acid sequence encoded by *Pantoea ananatis* c1705 gene
SEQ ID NO: 15: Nucleotide sequence of 5'-primer for disruption of c1129
SEQ ID NO: 16: Nucleotide sequence of 3'-primer for disruption of c1129
SEQ ID NO: 17: Nucleotide sequence of 5'-primer for detection of c1129 disruption
SEQ ID NO: 18: Nucleotide sequence of 3'-primer for detection of c1129 disruption
SEQ ID NO: 19: Nucleotide sequence of 5'-primer for disruption of c1705
SEQ ID NO: 20: Nucleotide sequence of 3'-primer for disruption of c1705
SEQ ID NO: 21: Nucleotide sequence of 5'-primer for detection of c1705 disruption
SEQ ID NO: 22: Nucleotide sequence of 3'-primer for detection of c1705 disruption While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A bacterium belonging to the Enterobacteriaceae family that is able to produce an L-amino acid selected from the group consisting of L-glutamic acid, L-arginine, L-threonine, and combinations thereof, and said bacterium is modified so that the activity of a protein encoded by ydcI gene is attenuated as compared to an unmodified bacterium.

2. The bacterium according to claim 1, wherein the activity of the protein encoded by ydcI gene is attenuated by decreasing the expression of the ydcI gene or by disrupting the ydcI gene.

3. The bacterium according to claim 1, wherein the protein encoded by ydcI gene is selected from the group consisting of:
   A) a protein comprising the amino acid sequence shown in SEQ ID NO: 2, 12 or 14; and
   B) a protein comprising the amino acid sequence shown in SEQ ID NO: 2, 12 or 14, except that one or several amino acids are substituted, deleted, inserted or added, and wherein said protein has DNA binding activity.

4. The bacterium according to claim 1, wherein said ydcI gene is selected from the group consisting of:
   (a) a DNA comprising the nucleotide sequence shown in 301-1221 of SEQ ID NO: 1, 301-1230 of SEQ ID NO: 11, or 301-1218 of SEQ ID NO: 13; and
   (b) a DNA which hybridizes under stringent conditions with a DNA comprising the nucleotide sequence shown in 301-1221 of SEQ ID NO: 1, 301-1230 of SEQ ID NO: 11, or 301-1218 of SEQ ID NO: 13, or with a probe which can be prepared from the same nucleotide sequence, said DNA encoding a protein having DNA binding activity.

5. The bacterium according to claim 1, wherein said bacterium belongs to the genus *Escherichia, Enterobacter* or *Pantoea*.

6. A method of producing an L-amino acid selected from the group consisting of L-glutamic acid, L-arginine, and L-threonine, comprising:
   A) culturing the bacterium according to claim 1 in a medium to allow the L-amino acid to be produced and accumulated in the medium or bacterium; and
   B) collecting the L-amino acid from the medium or bacterium.

* * * * *

```
                        SEQUENCE LISTING

<160> NUMBER OF SEQ ID NOS: 22

<210> SEQ ID NO 1
<211> LENGTH: 1524
<212> TYPE: DNA
<213> ORGANISM: Escherichia coli
<220> FEATURE:
<221> NAME/KEY: CDS
<222> LOCATION: (301)..(1221)

<400> SEQUENCE: 1
ttgcggaact tcttgctggt acatggctga cattgcctgc gaaaactgtt cccgaatctc     60
atccgccgtg atgctgttcg ccatagtgtc tgcctccagt ggtcagtaat ctggagtgta    120
ggtaaccgca ttcactcttg cgggaagaat ttacaaactg tgatctcgcc gcgaaaacat    180
caatattatc cattttgctg taacataatt gctttaattg ttaataatat tttgcaatca    240
agttatcata atcaaacaac ttcacttgtc agcgacaccg cttcgttttt aacatcgctt    300 atg gaa aaa aat agt ctg ttt agt cag cgc atc cgt ttg cgc cac ctt     348
Met Glu Lys Asn Ser Leu Phe Ser Gln Arg Ile Arg Leu Arg His Leu
1               5                  10                  15 cat aca ttc gta gct gtc gca caa caa gga act ttg ggg cgc gcg gct     396
His Thr Phe Val Ala Val Ala Gln Gln Gly Thr Leu Gly Arg Ala Ala
            20                  25                  30 gaa acc ctt aat ttg agt caa cct gcg ctc tct aag aca ttg aat gaa     444
Glu Thr Leu Asn Leu Ser Gln Pro Ala Leu Ser Lys Thr Leu Asn Glu
        35                  40                  45 ctg gag cag ctg act ggc gct cgc ttg ttt gag cgt ggt cgt cag ggg     492
Leu Glu Gln Leu Thr Gly Ala Arg Leu Phe Glu Arg Gly Arg Gln Gly
    50                  55                  60 gcg caa ctt acc tta ccc ggc gaa caa ttt tta acg cat gca gtc aga     540
Ala Gln Leu Thr Leu Pro Gly Glu Gln Phe Leu Thr His Ala Val Arg
65                  70                  75                  80 gtt ctt gac gcc atc aac act gcc gga cgg tcg ctt cat cgt aaa gaa     588
Val Leu Asp Ala Ile Asn Thr Ala Gly Arg Ser Leu His Arg Lys Glu
```

-continued

```
                            85                      90                      95
ggt ctt aat aat gat gtc gtc agg gtt ggt gca cta cct act gcg gca        636
Gly Leu Asn Asn Asp Val Val Arg Val Gly Ala Leu Pro Thr Ala Ala
            100                     105                     110 ctg ggg ata tta cct tcg gtt ata ggt cag ttt cat cag caa caa aaa        684
Leu Gly Ile Leu Pro Ser Val Ile Gly Gln Phe His Gln Gln Gln Lys
            115                     120                     125 gag acg acc ttg caa gtt gcg aca atg agt aac cct atg att ctg gcg        732
Glu Thr Thr Leu Gln Val Ala Thr Met Ser Asn Pro Met Ile Leu Ala
    130                     135                     140 ggt tta aaa acc ggg gaa atc gat atc ggc att ggt cgg atg tca gat        780
Gly Leu Lys Thr Gly Glu Ile Asp Ile Gly Ile Gly Arg Met Ser Asp
145                     150                     155                 160 cct gaa ctg atg acc ggg ctt aat tac gaa ctg ctg ttt ctt gaa tcg        828
Pro Glu Leu Met Thr Gly Leu Asn Tyr Glu Leu Leu Phe Leu Glu Ser
                165                     170                     175 ttg aag ctg gtt gtc cgc cct aat cac ccg cta ctt cag gag aac gta        876
Leu Lys Leu Val Val Arg Pro Asn His Pro Leu Leu Gln Glu Asn Val
            180                     185                     190 acg cta agc cgg gtg ctg gaa tgg ccg gtc gtt gta tca cca gaa ggc        924
Thr Leu Ser Arg Val Leu Glu Trp Pro Val Val Val Ser Pro Glu Gly
            195                     200                     205 act gcg cca cgc cag cat tca gat gca tta gtg cag agc cag ggc tgt        972
Thr Ala Pro Arg Gln His Ser Asp Ala Leu Val Gln Ser Gln Gly Cys
    210                     215                     220 aaa att cct tcg ggt tgt atc gaa acg ctg tct gct tcg cta tct cgt       1020
Lys Ile Pro Ser Gly Cys Ile Glu Thr Leu Ser Ala Ser Leu Ser Arg
225                     230                     235                 240 caa ctt acg gtt gaa tac gat tac gtg tgg ttt gtc cct tct ggc gct       1068
Gln Leu Thr Val Glu Tyr Asp Tyr Val Trp Phe Val Pro Ser Gly Ala
                245                     250                     255 gta aaa gac gac ctg cgt cat gcc acg ctg gtg gcc ctg cct gtt ccg       1116
Val Lys Asp Asp Leu Arg His Ala Thr Leu Val Ala Leu Pro Val Pro
            260                     265                     270 gga cat ggt gca ggc gaa ccg att gga ata ctg acc cgc gta gat gcg       1164
Gly His Gly Ala Gly Glu Pro Ile Gly Ile Leu Thr Arg Val Asp Ala
            275                     280                     285 acg ttc tct tct ggt tgc cag ttg atg att aac gct att cga aaa tca       1212
Thr Phe Ser Ser Gly Cys Gln Leu Met Ile Asn Ala Ile Arg Lys Ser
    290                     295                     300 atg ccg ttc tgaaaggtga agggatctgt cgatccctcc ttgaacattt              1261
Met Pro Phe
305 tcacaccgta gcgaaactaa ctggttcacc cgctccgcga ggttctgccg acacagaatg     1321 tttgtgcaga cggaatacat ccaccgcctc agtaatcgt gccgcctgtt cttcaaggga      1381 caccgccgcc gctgaggcct cttctaccag agaagcattc tgttgcgtca ccttatccat    1441 ttcagaaatc gcctggctaa cctgcgttat gcctctactt tgttcatccg aggcggcggc   1501 gatttcctgc atgatatgtg tga                                             1524

<210> SEQ ID NO 2
<211> LENGTH: 307
<212> TYPE: PRT
<213> ORGANISM: Escherichia coli

<400> SEQUENCE: 2

Met Glu Lys Asn Ser Leu Phe Ser Gln Arg Ile Arg Leu Arg His Leu
1               5                   10                  15

His Thr Phe Val Ala Val Ala Gln Gln Gly Thr Leu Gly Arg Ala Ala
```

```
            20                  25                  30
Glu Thr Leu Asn Leu Ser Gln Pro Ala Leu Ser Lys Thr Leu Asn Glu
            35                  40                  45
Leu Glu Gln Leu Thr Gly Ala Arg Leu Phe Glu Arg Gly Arg Gln Gly
        50                  55                  60
Ala Gln Leu Thr Leu Pro Gly Glu Gln Phe Leu Thr His Ala Val Arg
65                  70                  75                  80
Val Leu Asp Ala Ile Asn Thr Ala Gly Arg Ser Leu His Arg Lys Glu
                85                  90                  95
Gly Leu Asn Asn Asp Val Val Arg Val Gly Ala Leu Pro Thr Ala Ala
            100                 105                 110
Leu Gly Ile Leu Pro Ser Val Ile Gly Gln Phe His Gln Gln Gln Lys
            115                 120                 125
Glu Thr Thr Leu Gln Val Ala Thr Met Ser Asn Pro Met Ile Leu Ala
            130                 135                 140
Gly Leu Lys Thr Gly Glu Ile Asp Ile Gly Ile Gly Arg Met Ser Asp
145                 150                 155                 160
Pro Glu Leu Met Thr Gly Leu Asn Tyr Glu Leu Leu Phe Leu Glu Ser
                165                 170                 175
Leu Lys Leu Val Val Arg Pro Asn His Pro Leu Leu Gln Glu Asn Val
                180                 185                 190
Thr Leu Ser Arg Val Leu Glu Trp Pro Val Val Ser Pro Glu Gly
            195                 200                 205
Thr Ala Pro Arg Gln His Ser Asp Ala Leu Val Gln Ser Gln Gly Cys
            210                 215                 220
Lys Ile Pro Ser Gly Cys Ile Glu Thr Leu Ser Ala Ser Leu Ser Arg
225                 230                 235                 240
Gln Leu Thr Val Glu Tyr Asp Tyr Val Trp Phe Val Pro Ser Gly Ala
                245                 250                 255
Val Lys Asp Asp Leu Arg His Ala Thr Leu Val Ala Leu Pro Val Pro
                260                 265                 270
Gly His Gly Ala Gly Glu Pro Ile Gly Ile Leu Thr Arg Val Asp Ala
            275                 280                 285
Thr Phe Ser Ser Gly Cys Gln Leu Met Ile Asn Ala Ile Arg Lys Ser
    290                 295                 300
Met Pro Phe
305

<210> SEQ ID NO 3
<211> LENGTH: 101
<212> TYPE: DNA
<213> ORGANISM: Artificial sequence
<220> FEATURE:
<223> OTHER INFORMATION: attL

<400> SEQUENCE: 3 cctgctttt  tatactaagt  tggcattata  aaaaagcatt  gcttatcaat  ttgttgcaac    60
gaacaggtca  ctatcagtca  aaataaaatc  attatttgat  t                      101

<210> SEQ ID NO 4
<211> LENGTH: 172
<212> TYPE: DNA
<213> ORGANISM: Artificial sequence
<220> FEATURE:
<223> OTHER INFORMATION: attR

<400> SEQUENCE: 4
```

-continued

```
gcgctaatgc tctgttacag gtcactaata ccatctaagt agttgattca tagtgactgc    60
atatgttgtg ttttacagta ttatgtagtc tgtttttat gcaaaatcta atttaatata   120
ttgatattta tcatttta cgtttctcgt tcagctttt tatactaact tg            172
```

<210> SEQ ID NO 5
<211> LENGTH: 68
<212> TYPE: DNA
<213> ORGANISM: Artificial sequence
<220> FEATURE:
<223> OTHER INFORMATION: primer

<400> SEQUENCE: 5

```
aaggagggat cgacagatcc cttcaccttt cagaacggca ttgattttcg tgaagcctgc    60
tttttat                                                              68
```

<210> SEQ ID NO 6
<211> LENGTH: 68
<212> TYPE: DNA
<213> ORGANISM: Artificial sequence
<220> FEATURE:
<223> OTHER INFORMATION: primer

<400> SEQUENCE: 6

```
ggagtgtagg taaccgcatt cactcttgcg ggaagaattt acaaactgtg cgctcaagtt    60
agtataaa                                                             68
```

<210> SEQ ID NO 7
<211> LENGTH: 18
<212> TYPE: DNA
<213> ORGANISM: Artificial sequence
<220> FEATURE:
<223> OTHER INFORMATION: primer

<400> SEQUENCE: 7

```
tgcggaactt cttgctgg                                                  18
```

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8

```
tctgtgtcgg cagaacctcg                                                20
```

<210> SEQ ID NO 9
<211> LENGTH: 3774
<212> TYPE: DNA
<213> ORGANISM: Escherichia coli
<220> FEATURE:
<221> NAME/KEY: CDS
<222> LOCATION: (1)..(3771)

<400> SEQUENCE: 9

```
atg cta caa ctg ggg ctt agg cat aat cag cca acg acc aac gtt aca     48
Met Leu Gln Leu Gly Leu Arg His Asn Gln Pro Thr Thr Asn Val Thr
1               5                   10                  15 gtg gat aaa ata aag ctc aat aaa ccc tca aga agc aag gaa aag agg     96
Val Asp Lys Ile Lys Leu Asn Lys Pro Ser Arg Ser Lys Glu Lys Arg
            20                  25                  30 cga gta cct gcc gtg agc agc gct agt act ttc ggc cag aat gcg tgg    144
Arg Val Pro Ala Val Ser Ser Ala Ser Thr Phe Gly Gln Asn Ala Trp
        35                  40                  45
```

| | | |
|---|---|---|
| ctg gta gac gag atg ttc cag cag ttc cag aag gac ccc aag tcc gtg<br>Leu Val Asp Glu Met Phe Gln Gln Phe Gln Lys Asp Pro Lys Ser Val<br>50                          55                       60 | | 192 |
| gac aag gaa tgg aga gaa ctc ttt gag gcg cag ggg gga cca aat gct<br>Asp Lys Glu Trp Arg Glu Leu Phe Glu Ala Gln Gly Gly Pro Asn Ala<br>65                          70                       75                   80 | | 240 |
| acc ccc gct aca aca gaa gca cag cct tca gcg ccc aag gag tct gcg<br>Thr Pro Ala Thr Thr Glu Ala Gln Pro Ser Ala Pro Lys Glu Ser Ala<br>                     85                       90                   95 | | 288 |
| aaa cca gca cca aag gct gcc cct gca gcc aag gca gca ccg cgc gta<br>Lys Pro Ala Pro Lys Ala Ala Pro Ala Ala Lys Ala Ala Pro Arg Val<br>         100                     105                     110 | | 336 |
| gaa acc aag ccg gcc gcc aag acc gcc cct aag gcc aag gag tcc tca<br>Glu Thr Lys Pro Ala Ala Lys Thr Ala Pro Lys Ala Lys Glu Ser Ser<br>         115                     120                     125 | | 384 |
| gtg cca cag caa cct aag ctt ccg gag cca gga caa acc cca atc agg<br>Val Pro Gln Gln Pro Lys Leu Pro Glu Pro Gly Gln Thr Pro Ile Arg<br>130                         135                     140 | | 432 |
| ggt att ttc aag tcc atc gcg aag aac atg gat atc tcc ctg gaa atc<br>Gly Ile Phe Lys Ser Ile Ala Lys Asn Met Asp Ile Ser Leu Glu Ile<br>145                       150                     155                   160 | | 480 |
| cca acc gca acc tcg gtt cgc gat atg cca gct cgc ctc atg ttc gaa<br>Pro Thr Ala Thr Ser Val Arg Asp Met Pro Ala Arg Leu Met Phe Glu<br>                     165                     170                     175 | | 528 |
| aac cgc gcg atg gtc aac gat cag ctc aag cgc acc cgc ggt ggc aag<br>Asn Arg Ala Met Val Asn Asp Gln Leu Lys Arg Thr Arg Gly Gly Lys<br>         180                     185                     190 | | 576 |
| atc tcc ttc acc cac atc att ggc tac gcc atg gtg aag gca gtc atg<br>Ile Ser Phe Thr His Ile Ile Gly Tyr Ala Met Val Lys Ala Val Met<br>                195                     200                     205 | | 624 |
| gct cac ccg gac atg aac aac tcc tac gac gtc atc gac ggc aag cca<br>Ala His Pro Asp Met Asn Asn Ser Tyr Asp Val Ile Asp Gly Lys Pro<br>210                         215                     220 | | 672 |
| acc ctg atc gtg cct gag cac atc aac ctg ggc ctt gcc atc gac ctt<br>Thr Leu Ile Val Pro Glu His Ile Asn Leu Gly Leu Ala Ile Asp Leu<br>225                       230                     235                   240 | | 720 |
| cct cag aag gac ggc tcc cgc gca ctt gtc gta gca gcc atc aag gaa<br>Pro Gln Lys Asp Gly Ser Arg Ala Leu Val Val Ala Ala Ile Lys Glu<br>                245                     250                     255 | | 768 |
| acc gag aag atg aac ttc tcc gag ttc ctc gca gca tac gaa gac atc<br>Thr Glu Lys Met Asn Phe Ser Glu Phe Leu Ala Ala Tyr Glu Asp Ile<br>         260                     265                     270 | | 816 |
| gtg aca cgc tcc cgc aag ggc aag ctc acc atg gat gac tac cag ggc<br>Val Thr Arg Ser Arg Lys Gly Lys Leu Thr Met Asp Asp Tyr Gln Gly<br>                275                     280                     285 | | 864 |
| gtt acc gtt tcc ttg acc aac cca ggt ggc atc ggt acc cgc cac tct<br>Val Thr Val Ser Leu Thr Asn Pro Gly Gly Ile Gly Thr Arg His Ser<br>290                       295                     300 | | 912 |
| gtc cca cgt ctg acc aag ggc cag ggc acc atc atc ggt gtc ggt tcc<br>Val Pro Arg Leu Thr Lys Gly Gln Gly Thr Ile Ile Gly Val Gly Ser<br>305                       310                     315                   320 | | 960 |
| atg gat tac cca gca gag ttc cag ggc gct tcc gaa gac cgc ctt gca<br>Met Asp Tyr Pro Ala Glu Phe Gln Gly Ala Ser Glu Asp Arg Leu Ala<br>                     325                     330                     335 | | 1008 |
| gag ctc ggc gtt gga aag ctt gtc acc atc acc tcc acc tac gat cac<br>Glu Leu Gly Val Gly Lys Leu Val Thr Ile Thr Ser Thr Tyr Asp His<br>         340                     345                     350 | | 1056 |
| cgc gtg atc cag ggt gct gtg tcc ggt gaa ttc ctg cgt acc atg tct<br>Arg Val Ile Gln Gly Ala Val Ser Gly Glu Phe Leu Arg Thr Met Ser<br>                355                     360                     365 | | 1104 |

```
cgc ctg ctc acc gat gat tcc ttc tgg gat gag atc ttc gac gca atg    1152
Arg Leu Leu Thr Asp Asp Ser Phe Trp Asp Glu Ile Phe Asp Ala Met
    370                 375                 380 aac gtt cct tac acc cca atg cgt tgg gca cag gac gtt cca aac acc    1200
Asn Val Pro Tyr Thr Pro Met Arg Trp Ala Gln Asp Val Pro Asn Thr
385                 390                 395                 400 ggt gtt gat aag aac acc cgc gtc atg cag ctc att gag gca tac cgc    1248
Gly Val Asp Lys Asn Thr Arg Val Met Gln Leu Ile Glu Ala Tyr Arg
                405                 410                 415 tcc cgt gga cac ctc atc gct gac acc aac cca ctt tca tgg gtt cag    1296
Ser Arg Gly His Leu Ile Ala Asp Thr Asn Pro Leu Ser Trp Val Gln
            420                 425                 430 cct ggc atg cca gtt cca gac cac cgc gac ctc gac atc gag acc cac    1344
Pro Gly Met Pro Val Pro Asp His Arg Asp Leu Asp Ile Glu Thr His
        435                 440                 445 agc ctg acc atc tgg gat ctg gac cgt acc ttc agc gtc ggt ggc ttc    1392
Ser Leu Thr Ile Trp Asp Leu Asp Arg Thr Phe Ser Val Gly Gly Phe
    450                 455                 460 ggc ggc aag gag acc atg acc ctg cgc gag gta ctg tcc cgc ctg cgc    1440
Gly Gly Lys Glu Thr Met Thr Leu Arg Glu Val Leu Ser Arg Leu Arg
465                 470                 475                 480 gct gcc tac acc ttg aag gtc ggc tcc gaa tac acc cac atc ctg gac    1488
Ala Ala Tyr Thr Leu Lys Val Gly Ser Glu Tyr Thr His Ile Leu Asp
                485                 490                 495 cgc gac gag cgc acc tgg ctg cag gac cgc ctc gaa gcc gga atg cca    1536
Arg Asp Glu Arg Thr Trp Leu Gln Asp Arg Leu Glu Ala Gly Met Pro
            500                 505                 510 aag cca acc cag gca gag cag aag tac atc ctg cag aag ctg aac gcc    1584
Lys Pro Thr Gln Ala Glu Gln Lys Tyr Ile Leu Gln Lys Leu Asn Ala
        515                 520                 525 gca gag gct ttc gag aac ttc ctg cag acc aag tac gtc ggc cag aag    1632
Ala Glu Ala Phe Glu Asn Phe Leu Gln Thr Lys Tyr Val Gly Gln Lys
    530                 535                 540 cgc ttc tcc ctc gaa ggt gca gaa gct ctc atc cca ctg atg gac tcc    1680
Arg Phe Ser Leu Glu Gly Ala Glu Ala Leu Ile Pro Leu Met Asp Ser
545                 550                 555                 560 gcc atc gac acc gcc gca ggc cag ggc ctc gac gaa gtt gtc atc ggt    1728
Ala Ile Asp Thr Ala Ala Gly Gln Gly Leu Asp Glu Val Val Ile Gly
                565                 570                 575 atg cca cac cgt ggt cgc ctc aac gtg ctg ttc aac atc gtg ggc aag    1776
Met Pro His Arg Gly Arg Leu Asn Val Leu Phe Asn Ile Val Gly Lys
            580                 585                 590 cca ctg gca tcc atc ttc aac gag ttt gaa ggc caa atg gag cag ggc    1824
Pro Leu Ala Ser Ile Phe Asn Glu Phe Glu Gly Gln Met Glu Gln Gly
        595                 600                 605 cag atc ggt ggc tcc ggt gac gtg aag tac cac ctc ggt tcc gaa ggc    1872
Gln Ile Gly Gly Ser Gly Asp Val Lys Tyr His Leu Gly Ser Glu Gly
    610                 615                 620 cag cac ctg cag atg ttc ggc gac ggc gag atc aag gtc tcc ctg act    1920
Gln His Leu Gln Met Phe Gly Asp Gly Glu Ile Lys Val Ser Leu Thr
625                 630                 635                 640 gct aac ccg tcc cac ctg gaa gct gtt aac cca gtg atg gaa ggt atc    1968
Ala Asn Pro Ser His Leu Glu Ala Val Asn Pro Val Met Glu Gly Ile
                645                 650                 655 gtc cgc gca aag cag gac tac ctg gac aag ggc gta gac ggc aag act    2016
Val Arg Ala Lys Gln Asp Tyr Leu Asp Lys Gly Val Asp Gly Lys Thr
            660                 665                 670 gtt gtg cca ctg ctg ctc cac ggt gac gct gca ttc gca ggc ctg ggc    2064
Val Val Pro Leu Leu Leu His Gly Asp Ala Ala Phe Ala Gly Leu Gly
        675                 680                 685
```

```
atc gtg cca gaa acc atc aac ctg gct aag ctg cgt ggc tac gac gtc    2112
Ile Val Pro Glu Thr Ile Asn Leu Ala Lys Leu Arg Gly Tyr Asp Val
690             695                 700 gga ggc acc atc cac atc gtg gtg aac aac cag atc ggc ttc acc acc    2160
Gly Gly Thr Ile His Ile Val Val Asn Asn Gln Ile Gly Phe Thr Thr
705             710                 715                 720 acc cca gac tcc agc cgc tcc atg cac tac gca acc gac tac gcc aag    2208
Thr Pro Asp Ser Ser Arg Ser Met His Tyr Ala Thr Asp Tyr Ala Lys
                725                 730                 735 gca ttc ggc tgc cca gtc ttc cac gtc aat ggt gat gac cca gag gca    2256
Ala Phe Gly Cys Pro Val Phe His Val Asn Gly Asp Asp Pro Glu Ala
            740                 745                 750 gtt gtc tgg gtt ggc cag ctg gca acc gag tac cgt cgt cgc ttc ggc    2304
Val Val Trp Val Gly Gln Leu Ala Thr Glu Tyr Arg Arg Arg Phe Gly
            755                 760                 765 aag gac gtc ttc atc gac ctc gtt tgc tac cgc ctc cgc ggc cac aac    2352
Lys Asp Val Phe Ile Asp Leu Val Cys Tyr Arg Leu Arg Gly His Asn
770             775                 780 gaa gct gat gat cct tcc atg acc cag cca aag atg tat gag ctc atc    2400
Glu Ala Asp Asp Pro Ser Met Thr Gln Pro Lys Met Tyr Glu Leu Ile
785             790                 795                 800 acc ggc cgc gag acc gtt cgt gct cag tac acc gaa gac ctg ctc gga    2448
Thr Gly Arg Glu Thr Val Arg Ala Gln Tyr Thr Glu Asp Leu Leu Gly
                805                 810                 815 cgt gga gac ctc tcc aac gaa gat gca gaa gca gtc gtc cgc gac ttc    2496
Arg Gly Asp Leu Ser Asn Glu Asp Ala Glu Ala Val Val Arg Asp Phe
            820                 825                 830 cac gac cag atg gaa tct gtg ttc aac gaa gtc aag gaa ggc ggc aag    2544
His Asp Gln Met Glu Ser Val Phe Asn Glu Val Lys Glu Gly Gly Lys
            835                 840                 845 aag cag gct gag gca cag acc ggc atc acc ggc tcc cag aag ctt cca    2592
Lys Gln Ala Glu Ala Gln Thr Gly Ile Thr Gly Ser Gln Lys Leu Pro
850             855                 860 cac ggc ctt gag acc aac atc tcc cgt gaa gag ctc ctg gaa ctg gga    2640
His Gly Leu Glu Thr Asn Ile Ser Arg Glu Glu Leu Leu Glu Leu Gly
865             870                 875                 880 cag gct ttc gcc aac acc cca gaa ggc ttc aac tac cac cca cgt gtg    2688
Gln Ala Phe Ala Asn Thr Pro Glu Gly Phe Asn Tyr His Pro Arg Val
                885                 890                 895 gct cca gtt gct aag aag cgc gtc tcc tct gtc acc gaa ggt ggc atc    2736
Ala Pro Val Ala Lys Lys Arg Val Ser Ser Val Thr Glu Gly Gly Ile
            900                 905                 910 gac tgg gca tgg ggc gag ctc ctc gcc ttc ggt tcc ctg gct aac tcc    2784
Asp Trp Ala Trp Gly Glu Leu Leu Ala Phe Gly Ser Leu Ala Asn Ser
            915                 920                 925 ggc cgc ttg gtt cgc ctt gca ggt gaa gat tcc cgc cgc ggt acc ttc    2832
Gly Arg Leu Val Arg Leu Ala Gly Glu Asp Ser Arg Arg Gly Thr Phe
930             935                 940 acc cag cgc cac gca gtt gcc atc gac cca gcg acc gct gaa gag ttc    2880
Thr Gln Arg His Ala Val Ala Ile Asp Pro Ala Thr Ala Glu Glu Phe
945             950                 955                 960 aac cca ctc cac gag ctt gca cag tcc aag ggc aac aac ggt aag ttc    2928
Asn Pro Leu His Glu Leu Ala Gln Ser Lys Gly Asn Asn Gly Lys Phe
                965                 970                 975 ctg gtc tac aac tcc gca ctg acc gag tac gca ggc atg ggc ttc gag    2976
Leu Val Tyr Asn Ser Ala Leu Thr Glu Tyr Ala Gly Met Gly Phe Glu
            980                 985                 990 tac ggc tac tcc gta gga aac gaa    gac tcc gtc gtt gca    tgg gaa gca    3024
Tyr Gly Tyr Ser Val Gly Asn Glu    Asp Ser Val Val Ala    Trp Glu Ala
            995                    1000                   1005
```

```
cag ttc ggc gac ttc gcc aac ggc gct cag acc atc atc gat gag      3069
Gln Phe Gly Asp Phe Ala Asn Gly Ala Gln Thr Ile Ile Asp Glu
    1010                1015                1020 tac gtc tcc tca ggc gaa gct aag tgg ggc cag acc tcc aag ctg      3114
Tyr Val Ser Ser Gly Glu Ala Lys Trp Gly Gln Thr Ser Lys Leu
1025                1030                1035 atc ctt ctg ctg cct cac ggc tac gaa ggc cag ggc cca gac cac      3159
Ile Leu Leu Leu Pro His Gly Tyr Glu Gly Gln Gly Pro Asp His
    1040                1045                1050 tct tcc gca cgt atc gag cgc ttc ctg cag ctg tgc gct gag ggt      3204
Ser Ser Ala Arg Ile Glu Arg Phe Leu Gln Leu Cys Ala Glu Gly
1055                1060                1065 tcc atg act gtt gct cag cca tcc acc cca gca aac cac ttc cac      3249
Ser Met Thr Val Ala Gln Pro Ser Thr Pro Ala Asn His Phe His
    1070                1075                1080 ctg ctg cgt cgt cac gct ctg tcc gac ctg aag cgt cca ctg gtt      3294
Leu Leu Arg Arg His Ala Leu Ser Asp Leu Lys Arg Pro Leu Val
1085                1090                1095 atc ttc acc ccg aag tcc atg ctg cgt aac aag gct gct gcc tcc      3339
Ile Phe Thr Pro Lys Ser Met Leu Arg Asn Lys Ala Ala Ala Ser
    1100                1105                1110 gca cca gaa gac ttc act gag gtc acc aag ttc caa tcc gtg atc      3384
Ala Pro Glu Asp Phe Thr Glu Val Thr Lys Phe Gln Ser Val Ile
1115                1120                1125 gac gat cca aac gtt gca gat gca gcc aag gtg aag aag gtc atg      3429
Asp Asp Pro Asn Val Ala Asp Ala Ala Lys Val Lys Lys Val Met
    1130                1135                1140 ctg gtc tcc ggc aag ctg tac tac gaa ttg gca aag cgc aag gag      3474
Leu Val Ser Gly Lys Leu Tyr Tyr Glu Leu Ala Lys Arg Lys Glu
1145                1150                1155 aag gac gga cgc gac gac atc gcg atc gtt cgt atc gaa atg ctc      3519
Lys Asp Gly Arg Asp Asp Ile Ala Ile Val Arg Ile Glu Met Leu
    1160                1165                1170 cac cca att ccg ttc aac cgc atc tcc gag gct ctt gcc ggc tac      3564
His Pro Ile Pro Phe Asn Arg Ile Ser Glu Ala Leu Ala Gly Tyr
1175                1180                1185 cct aac gct gag gaa gtc ctc ttc gtt cag gat gag cca gca aac      3609
Pro Asn Ala Glu Glu Val Leu Phe Val Gln Asp Glu Pro Ala Asn
    1190                1195                1200 cag ggc cca tgg ccg ttc tac cag gag cac ctc cca gag ctg atc      3654
Gln Gly Pro Trp Pro Phe Tyr Gln Glu His Leu Pro Glu Leu Ile
1205                1210                1215 ccg aac atg cca aag atg cgc cgc gtt tcc cgc cgc gct cag tcc      3699
Pro Asn Met Pro Lys Met Arg Arg Val Ser Arg Arg Ala Gln Ser
    1220                1225                1230 tcc acc gca act ggt gtt gct aag gtg cac cag ctg gag gag aag      3744
Ser Thr Ala Thr Gly Val Ala Lys Val His Gln Leu Glu Glu Lys
1235                1240                1245 cag ctt atc gac gag gct ttc gag gct taa                          3774
Gln Leu Ile Asp Glu Ala Phe Glu Ala
    1250                1255
```

<210> SEQ ID NO 10
<211> LENGTH: 1257
<212> TYPE: PRT
<213> ORGANISM: Escherichia coli

<400> SEQUENCE: 10

```
Met Leu Gln Leu Gly Leu Arg His Asn Gln Pro Thr Thr Asn Val Thr
1               5                   10                  15
```

```
Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
            35                  40                  45

Leu Val Asp Glu Met Phe Gln Gln Phe Gln Lys Asp Pro Lys Ser Val
 50                  55                  60

Asp Lys Glu Trp Arg Glu Leu Phe Glu Ala Gln Gly Gly Pro Asn Ala
 65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
            115                 120                 125

Val Pro Gln Gln Pro Lys Leu Pro Glu Pro Gly Gln Thr Pro Ile Arg
            130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
            195                 200                 205

Ala His Pro Asp Met Asn Asn Ser Tyr Asp Val Ile Asp Gly Lys Pro
 210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
            275                 280                 285

Val Thr Val Ser Leu Thr Asn Pro Gly Gly Ile Gly Thr Arg His Ser
 290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
            355                 360                 365

Arg Leu Leu Thr Asp Asp Ser Phe Trp Asp Glu Ile Phe Asp Ala Met
            370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
            435                 440                 445
```

-continued

Ser Leu Thr Ile Trp Asp Leu Asp Arg Thr Phe Ser Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
        515                 520                 525

Ala Glu Ala Phe Glu Asn Phe Leu Gln Thr Lys Tyr Val Gly Gln Lys
    530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
        595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu Leu His Gly Asp Ala Ala Phe Ala Gly Leu Gly
        675                 680                 685

Ile Val Pro Glu Thr Ile Asn Leu Ala Lys Leu Arg Gly Tyr Asp Val
    690                 695                 700

Gly Gly Thr Ile His Ile Val Val Asn Asn Gln Ile Gly Phe Thr Thr
705                 710                 715                 720

Thr Pro Asp Ser Ser Arg Ser Met His Tyr Ala Thr Asp Tyr Ala Lys
                725                 730                 735

Ala Phe Gly Cys Pro Val Phe His Val Asn Gly Asp Asp Pro Glu Ala
            740                 745                 750

Val Val Trp Val Gly Gln Leu Ala Thr Glu Tyr Arg Arg Arg Phe Gly
        755                 760                 765

Lys Asp Val Phe Ile Asp Leu Val Cys Tyr Arg Leu Arg Gly His Asn
    770                 775                 780

Glu Ala Asp Asp Pro Ser Met Thr Gln Pro Lys Met Tyr Glu Leu Ile
785                 790                 795                 800

Thr Gly Arg Glu Thr Val Arg Ala Gln Tyr Thr Glu Asp Leu Leu Gly
                805                 810                 815

Arg Gly Asp Leu Ser Asn Glu Asp Ala Glu Ala Val Val Arg Asp Phe
            820                 825                 830

His Asp Gln Met Glu Ser Val Phe Asn Glu Val Lys Glu Gly Gly Lys
        835                 840                 845

Lys Gln Ala Glu Ala Gln Thr Gly Ile Thr Gly Ser Gln Lys Leu Pro
    850                 855                 860

His Gly Leu Glu Thr Asn Ile Ser Arg Glu Glu Leu Leu Glu Leu Gly

```
                865                 870                 875                 880
Gln Ala Phe Ala Asn Thr Pro Glu Gly Phe Asn Tyr His Pro Arg Val
                    885                 890                 895
Ala Pro Val Ala Lys Lys Arg Val Ser Ser Val Thr Glu Gly Gly Ile
        900                 905                 910
Asp Trp Ala Trp Gly Glu Leu Leu Ala Phe Gly Ser Leu Ala Asn Ser
        915                 920                 925
Gly Arg Leu Val Arg Leu Ala Gly Glu Asp Ser Arg Arg Gly Thr Phe
        930                 935                 940
Thr Gln Arg His Ala Val Ala Ile Asp Pro Ala Thr Ala Glu Glu Phe
945                 950                 955                 960
Asn Pro Leu His Glu Leu Ala Gln Ser Lys Gly Asn Asn Gly Lys Phe
                    965                 970                 975
Leu Val Tyr Asn Ser Ala Leu Thr Glu Tyr Ala Gly Met Gly Phe Glu
                980                 985                 990
Tyr Gly Tyr Ser Val Gly Asn Glu Asp Ser Val Val Ala Trp Glu Ala
            995                 1000                1005
Gln Phe Gly Asp Phe Ala Asn Gly Ala Gln Thr Ile Ile Asp Glu
    1010                1015                1020
Tyr Val Ser Ser Gly Glu Ala Lys Trp Gly Gln Thr Ser Lys Leu
    1025                1030                1035
Ile Leu Leu Pro His Gly Tyr Glu Gly Gln Gly Pro Asp His
    1040                1045                1050
Ser Ser Ala Arg Ile Glu Arg Phe Leu Gln Leu Cys Ala Glu Gly
    1055                1060                1065
Ser Met Thr Val Ala Gln Pro Ser Thr Pro Ala Asn His Phe His
    1070                1075                1080
Leu Leu Arg Arg His Ala Leu Ser Asp Leu Lys Arg Pro Leu Val
    1085                1090                1095
Ile Phe Thr Pro Lys Ser Met Leu Arg Asn Lys Ala Ala Ala Ser
    1100                1105                1110
Ala Pro Glu Asp Phe Thr Glu Val Thr Lys Phe Gln Ser Val Ile
    1115                1120                1125
Asp Asp Pro Asn Val Ala Asp Ala Ala Lys Val Lys Lys Val Met
    1130                1135                1140
Leu Val Ser Gly Lys Leu Tyr Tyr Glu Leu Ala Lys Arg Lys Glu
    1145                1150                1155
Lys Asp Gly Arg Asp Asp Ile Ala Ile Val Arg Ile Glu Met Leu
    1160                1165                1170
His Pro Ile Pro Phe Asn Arg Ile Ser Glu Ala Leu Ala Gly Tyr
    1175                1180                1185
Pro Asn Ala Glu Glu Val Leu Phe Val Gln Asp Glu Pro Ala Asn
    1190                1195                1200
Gln Gly Pro Trp Pro Phe Tyr Gln Glu His Leu Pro Glu Leu Ile
    1205                1210                1215
Pro Asn Met Pro Lys Met Arg Arg Val Ser Arg Arg Ala Gln Ser
    1220                1225                1230
Ser Thr Ala Thr Gly Val Ala Lys Val His Gln Leu Glu Glu Lys
    1235                1240                1245
Gln Leu Ile Asp Glu Ala Phe Glu Ala
    1250                1255

<210> SEQ ID NO 11
<211> LENGTH: 1533
```

<212> TYPE: DNA
<213> ORGANISM: Pantoea ananatis
<220> FEATURE:
<221> NAME/KEY: CDS
<222> LOCATION: (301)..(1230)

<400> SEQUENCE: 11

```
atggcgccgc atcttaacct gtggattgtg gcgcgcggca ttaacatcgg actgaacacc      60
cggctctact tcgctgatga acaggcggca aatgacgccg atccggtgct gaatgtgatc     120
gaatgggaga agcgacgtcg caccttgctg gcgcggcgtg agcagcgcgg cgacgagacg     180
gtctaccggt tcgatatctg gctgcagggt gaaaacgaaa ccgtgttctt tgatgtctga     240
accttaatct gcccacgaca atgtccttgc cgcttcggcg gcaaattcat aacatgagtc     300
```

| | | | | | | | | | | | | | | | | |
|---|---|---|---|---|---|---|---|---|---|---|---|---|---|---|---|---|
| atg | gat | agg | gtt | tcc | cgg | ttt | agt | cag | cgc | gtg | cgc | gtg | cgc | cat | ctt | 348 |
| Met | Asp | Arg | Val | Ser | Arg | Phe | Ser | Gln | Arg | Val | Arg | Val | Arg | His | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | gct | ttt | gtg | gcc | act | gca | cag | cag | ggg | acg | ctg | ggg | cgc | gcc | gcg | 396 |
| His | Ala | Phe | Val | Ala | Thr | Ala | Gln | Gln | Gly | Thr | Leu | Gly | Arg | Ala | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| ctc | cat | ctg | ggg | att | acc | cag | ccc | gcc | ctg | tcc | aag | acc | ctc | aac | gaa | 444 |
| Leu | His | Leu | Gly | Ile | Thr | Gln | Pro | Ala | Leu | Ser | Lys | Thr | Leu | Asn | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| ctc | gaa | tac | ctt | gcc | ggt | gag | acg | ctg | ttg | ctg | cgc | agc | cgc | cag | ggg | 492 |
| Leu | Glu | Tyr | Leu | Ala | Gly | Glu | Thr | Leu | Leu | Leu | Arg | Ser | Arg | Gln | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| acg | gaa | ctc | acc | gcc | agc | ggc | acg | cga | ttc | ctg | cac | gat | gcc | atc | cgt | 540 |
| Thr | Glu | Leu | Thr | Ala | Ser | Gly | Thr | Arg | Phe | Leu | His | Asp | Ala | Ile | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| att | ctt | gat | gcg | ctg | aat | att | gtg | gac | cag | gtg | atg | cgt | ccc | ggc | agt | 588 |
| Ile | Leu | Asp | Ala | Leu | Asn | Ile | Val | Asp | Gln | Val | Met | Arg | Pro | Gly | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| gcg | ccg | cag | ccc | gga | ccg | atg | cat | att | ggc | gca | ctg | cct | acc | gcc | att | 636 |
| Ala | Pro | Gln | Pro | Gly | Pro | Met | His | Ile | Gly | Ala | Leu | Pro | Thr | Ala | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| gtc | agc | gtg | gtg | gcg | ccg | gta | tta | gcc | agc | ctg | cag | cag | cac | tat | ccg | 684 |
| Val | Ser | Val | Val | Ala | Pro | Val | Leu | Ala | Ser | Leu | Gln | Gln | His | Tyr | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| ggc | tgg | cgc | att | cag | gtc | agc | acg | ctg | gcg | aat | gat | gcg | ttg | ctg | atg | 732 |
| Gly | Trp | Arg | Ile | Gln | Val | Ser | Thr | Leu | Ala | Asn | Asp | Ala | Leu | Leu | Met | |
| | 130 | | | | | 135 | | | | | 140 | | | | | |

| | | | | | | | | | | | | | | | | |
|---|---|---|---|---|---|---|---|---|---|---|---|---|---|---|---|---|
| ggg | ata | aaa | tca | ggg | cag | atg | gcg | ctg | ggg | att | ggg | cgc | atg | gct | gaa | 780 |
| Gly | Ile | Lys | Ser | Gly | Gln | Met | Ala | Leu | Gly | Ile | Gly | Arg | Met | Ala | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ccc | gta | ttg | atg | gat | ggc | ctg | aac | ttc | gag | ctg | ctg | tat | ctg | gaa | acc | 828 |
| Pro | Val | Leu | Met | Asp | Gly | Leu | Asn | Phe | Glu | Leu | Leu | Tyr | Leu | Glu | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| ctg | cgt | ctg | gtt | gtg | gcc | cca | cat | cat | cct | ctg | ctg | cat | gct | ggc | gta | 876 |
| Leu | Arg | Leu | Val | Val | Ala | Pro | His | His | Pro | Leu | Leu | His | Ala | Gly | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| acg | ctg | gct | gaa | gcc | ctg | agc | tgg | ccg | ctg | atc | ctg | tcg | cca | cgc | ggc | 924 |
| Thr | Leu | Ala | Glu | Ala | Leu | Ser | Trp | Pro | Leu | Ile | Leu | Ser | Pro | Arg | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| acg | gtg | ccg | cgc | cag | aat | gcc | gaa | tca | ctg | atg | acc | agc | cat | ggc | ctg | 972 |
| Thr | Val | Pro | Arg | Gln | Asn | Ala | Glu | Ser | Leu | Met | Thr | Ser | His | Gly | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| aga | tta | ccg | gat | ggc | gca | gtg | gaa | acc | ctg | tca | acc | acg | ctg | gcc | cgc | 1020 |
| Arg | Leu | Pro | Asp | Gly | Ala | Val | Glu | Thr | Leu | Ser | Thr | Thr | Leu | Ala | Arg | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgt | ctg | acg | ctg | agt | cac | ggc | tac | gtc | tgg | ctg | gtg | ccc | tac | ggc | gcg | 1068 |
| Arg | Leu | Thr | Leu | Ser | His | Gly | Tyr | Val | Trp | Leu | Val | Pro | Tyr | Gly | Ala | |

```
                        245                 250                 255
gtg cgc gac gac ctg acc agc aac cag ctt cgc acg ttg ccg ctt ccc    1116
Val Arg Asp Asp Leu Thr Ser Asn Gln Leu Arg Thr Leu Pro Leu Pro
            260                 265                 270 agc cag ggg atg gct gag gcg gtc ggc atc ctg acc cgc cag cag cac    1164
Ser Gln Gly Met Ala Glu Ala Val Gly Ile Leu Thr Arg Gln Gln His
275                 280                 285 gcg cca cca ccc gag cag ctg cag ctg gtg gcg gcc ttg cgg caa cgg    1212
Ala Pro Pro Pro Glu Gln Leu Gln Leu Val Ala Ala Leu Arg Gln Arg
            290                 295                 300 gtg ctg gac gtg cct gtc tgacagcgca gtttactggg cgctgtcctg           1260
Val Leu Asp Val Pro Val
305                 310 ctcatcgaaa acgctctgcg ccagatggaa cgcggcgttg gatgctggca ggccgcagta   1320
gagcgcagaa tgcatcagca actctttgat tcatcccgg ctgacgccgt tattgaacgc    1380
ggcccgcagg tgcatcttca gctccgcttc gcggttgagc gcaatcagca tgccgatggt   1440
gatcaggctg cgcgtgtggc gagtcaggcc aggccgggtc caaatctcgc cccaggcgta   1500
gcggctgata aagttctgga attcgtcatt cag                                1533

<210> SEQ ID NO 12
<211> LENGTH: 310
<212> TYPE: PRT
<213> ORGANISM: Pantoea ananatis

<400> SEQUENCE: 12

Met Asp Arg Val Ser Arg Phe Ser Gln Arg Val Arg Val Arg His Leu
1               5                   10                  15

His Ala Phe Val Ala Thr Ala Gln Gln Gly Thr Leu Gly Arg Ala Ala
            20                  25                  30

Leu His Leu Gly Ile Thr Gln Pro Ala Leu Ser Lys Thr Leu Asn Glu
        35                  40                  45

Leu Glu Tyr Leu Ala Gly Glu Thr Leu Leu Arg Ser Arg Gln Gly
    50                  55                  60

Thr Glu Leu Thr Ala Ser Gly Thr Arg Phe Leu His Asp Ala Ile Arg
65                  70                  75                  80

Ile Leu Asp Ala Leu Asn Ile Val Asp Gln Val Met Arg Pro Gly Ser
                85                  90                  95

Ala Pro Gln Pro Gly Pro Met His Ile Gly Ala Leu Pro Thr Ala Ile
            100                 105                 110

Val Ser Val Val Ala Pro Val Leu Ala Ser Leu Gln Gln His Tyr Pro
        115                 120                 125

Gly Trp Arg Ile Gln Val Ser Thr Leu Ala Asn Asp Ala Leu Leu Met
    130                 135                 140

Gly Ile Lys Ser Gly Gln Met Ala Leu Gly Ile Gly Arg Met Ala Glu
145                 150                 155                 160

Pro Val Leu Met Asp Gly Leu Asn Phe Glu Leu Leu Tyr Leu Glu Thr
                165                 170                 175

Leu Arg Leu Val Val Ala Pro His His Pro Leu Leu His Ala Gly Val
            180                 185                 190

Thr Leu Ala Glu Ala Leu Ser Trp Pro Leu Ile Leu Ser Pro Arg Gly
        195                 200                 205

Thr Val Pro Arg Gln Asn Ala Glu Ser Leu Met Thr Ser His Gly Leu
    210                 215                 220

Arg Leu Pro Asp Gly Ala Val Glu Thr Leu Ser Thr Thr Leu Ala Arg
225                 230                 235                 240
```

```
Arg Leu Thr Leu Ser His Gly Tyr Val Trp Leu Val Pro Tyr Gly Ala
            245                 250                 255

Val Arg Asp Asp Leu Thr Ser Asn Gln Leu Arg Thr Leu Pro Leu Pro
        260                 265                 270

Ser Gln Gly Met Ala Glu Ala Val Gly Ile Leu Thr Arg Gln Gln His
            275                 280                 285

Ala Pro Pro Glu Gln Leu Gln Leu Val Ala Ala Leu Arg Gln Arg
        290                 295                 300

Val Leu Asp Val Pro Val
305             310

<210> SEQ ID NO 13
<211> LENGTH: 1521
<212> TYPE: DNA
<213> ORGANISM: Pantoea ananatis
<220> FEATURE:
<221> NAME/KEY: CDS
<222> LOCATION: (301)..(1218)

<400> SEQUENCE: 13
gaaataacta tcagttttgg taaaaaaaac ggcgcttatg atagccgatc gttaacgata      60
aaacgcgtga atttacacg agaataataa tcattcaaaa aatggttagt taagttaatg     120
atttttcagt cacgactggc ggctgcgtta tccgacgata gcgcctcaag cattattat     180 cagtaactta aatgaaaacc cgataaaaag tacacattgt taataaaaat ttgcagcaaa     240
gttaacaaaa tccagcttaa atagttgcca gttacctggc aatgtcatta agtttgggaa     300 atg gaa aaa aat atc ctt ttc aat cag cgc att cgc ttg cgt cat tta      348
Met Glu Lys Asn Ile Leu Phe Asn Gln Arg Ile Arg Leu Arg His Leu
1               5                   10                  15 cat gcc ttt gtt gcc gtt gcg cag cag gga acg ctg ggg cgt gca gcc      396
His Ala Phe Val Ala Val Ala Gln Gln Gly Thr Leu Gly Arg Ala Ala
                20                  25                  30 gag acg tta agt ctt agc cag cct gca ctc tct aaa acc ctt aac gaa      444
Glu Thr Leu Ser Leu Ser Gln Pro Ala Leu Ser Lys Thr Leu Asn Glu
            35                  40                  45 ctc gag gaa ctg acg ggc gtc agg ctg ttc gaa cgc ggc cga ctg ggc      492
Leu Glu Glu Leu Thr Gly Val Arg Leu Phe Glu Arg Gly Arg Leu Gly
        50                  55                  60 gca cag ctc acc acc atg gga gag cag ttt ctg acg cat gcg gta aag      540
Ala Gln Leu Thr Thr Met Gly Glu Gln Phe Leu Thr His Ala Val Lys
65                  70                  75                  80 gtg ctg gat gca ctg aac cat gcc ggt cag agc ttt aac gaa cag atc      588
Val Leu Asp Ala Leu Asn His Ala Gly Gln Ser Phe Asn Glu Gln Ile
                85                  90                  95 aac gag cgt cct gcc gtg att cgg ctt ggc gcg ctt acg act gcc gcg      636
Asn Glu Arg Pro Ala Val Ile Arg Leu Gly Ala Leu Thr Thr Ala Ala
                100                 105                 110 atg ggc atg ttg cca cag att ctc gat cgc ttt cat caa ctg cgt cct      684
Met Gly Met Leu Pro Gln Ile Leu Asp Arg Phe His Gln Leu Arg Pro
            115                 120                 125 aac acc acc att cag gtt gcc acg ttg cac aac aat gtc ttg ctg gcc      732
Asn Thr Thr Ile Gln Val Ala Thr Leu His Asn Asn Val Leu Leu Ala
        130                 135                 140 gga ctg cgc gcg ggc gaa ttt gat atc ggc att ggt cgt atg gct gat      780
Gly Leu Arg Ala Gly Glu Phe Asp Ile Gly Ile Gly Arg Met Ala Asp
145                 150                 155                 160 aaa gag atg atg acc ggc tta acc tat gaa ctg ctg ttc ctc gaa tca      828
Lys Glu Met Met Thr Gly Leu Thr Tyr Glu Leu Leu Phe Leu Glu Ser
                165                 170                 175
```

-continued

```
tta aaa ctg gtt gtc agg ccg gaa cat ccc ctg tta agt gac aac gtc    876
Leu Lys Leu Val Val Arg Pro Glu His Pro Leu Leu Ser Asp Asn Val
            180                 185                 190 acc tta tcc cgc gcc atg cag tgg ccg gta gtg att tcc ccc gaa ggg    924
Thr Leu Ser Arg Ala Met Gln Trp Pro Val Val Ile Ser Pro Glu Gly
        195                 200                 205 acg gct ccg cgc cgc ctg gcc cag cag atg ctt gac gag cag ggc tgc    972
Thr Ala Pro Arg Arg Leu Ala Gln Gln Met Leu Asp Glu Gln Gly Cys
    210                 215                 220 tgt tta ccg cca cat tgc gtt gaa acc tct tcc act tcg ctg gcc cgc   1020
Cys Leu Pro Pro His Cys Val Glu Thr Ser Ser Thr Ser Leu Ala Arg
225                 230                 235                 240 caa ctg gcg cta cgc tat gac tac atc tgg ttt gtg cct tca ggc gcc   1068
Gln Leu Ala Leu Arg Tyr Asp Tyr Ile Trp Phe Val Pro Ser Gly Ala
                245                 250                 255 att aaa gaa gat ctc agt cac aac gcc gtc ttc tcg ctg ccc att acc   1116
Ile Lys Glu Asp Leu Ser His Asn Ala Val Phe Ser Leu Pro Ile Thr
            260                 265                 270 tct cca ggc cct ggc gag ccg gtc ggt att atc acc cgg acc ggc gat   1164
Ser Pro Gly Pro Gly Glu Pro Val Gly Ile Ile Thr Arg Thr Gly Asp
        275                 280                 285 acc tta agc ctg agc gct gag gtt ctg atg agt act att cgt aaa ttt   1212
Thr Leu Ser Leu Ser Ala Glu Val Leu Met Ser Thr Ile Arg Lys Phe
    290                 295                 300 cac agt tagcgactgc gttttgcatg tcgctcccag ttgtcctgac gcgctttctc   1268
His Ser
305 ggtcttacgt aatccgacgt aaagcgcgcc cgccccgccg tgctgctttt gcgccacaca   1328 gaaggtctgc acctcatcca gctcccgtag ccaacgatcc agataacttc gtacgatgtt   1388 ggcgtgggat tcactgtcgc gcccttacc gtgaatgata agcaggttgc gaaacccggc    1448 ttgccgcacc tcacgaatga aattaaacag gttctggcga cagacctcta caggctgacg    1508 cagtaaaatta agg                                                     1521
```

<210> SEQ ID NO 14
<211> LENGTH: 306
<212> TYPE: PRT
<213> ORGANISM: Pantoea ananatis

<400> SEQUENCE: 14

```
Met Glu Lys Asn Ile Leu Phe Asn Gln Arg Ile Arg Leu Arg His Leu
1               5                   10                  15

His Ala Phe Val Ala Val Ala Gln Gln Gly Thr Leu Gly Arg Ala Ala
            20                  25                  30

Glu Thr Leu Ser Leu Ser Gln Pro Ala Leu Ser Lys Thr Leu Asn Glu
        35                  40                  45

Leu Glu Glu Leu Thr Gly Val Arg Leu Phe Glu Arg Gly Arg Leu Gly
    50                  55                  60

Ala Gln Leu Thr Thr Met Gly Glu Gln Phe Leu Thr His Ala Val Lys
65                  70                  75                  80

Val Leu Asp Ala Leu Asn His Ala Gly Gln Ser Phe Asn Glu Gln Ile
                85                  90                  95

Asn Glu Arg Pro Ala Val Ile Arg Leu Gly Ala Leu Thr Thr Ala Ala
            100                 105                 110

Met Gly Met Leu Pro Gln Ile Leu Asp Arg Phe His Gln Leu Arg Pro
        115                 120                 125

Asn Thr Thr Ile Gln Val Ala Thr Leu His Asn Asn Val Leu Leu Ala
```

```
            130                 135                 140
Gly Leu Arg Ala Gly Glu Phe Asp Ile Gly Ile Gly Arg Met Ala Asp
145                 150                 155                 160

Lys Glu Met Met Thr Gly Leu Thr Tyr Glu Leu Phe Leu Glu Ser
                165                 170                 175

Leu Lys Leu Val Val Arg Pro Glu His Pro Leu Leu Ser Asp Asn Val
            180                 185                 190

Thr Leu Ser Arg Ala Met Gln Trp Pro Val Val Ile Ser Pro Glu Gly
        195                 200                 205

Thr Ala Pro Arg Arg Leu Ala Gln Gln Met Leu Asp Glu Gln Gly Cys
    210                 215                 220

Cys Leu Pro Pro His Cys Val Glu Thr Ser Ser Thr Ser Leu Ala Arg
225                 230                 235                 240

Gln Leu Ala Leu Arg Tyr Asp Tyr Ile Trp Phe Val Pro Ser Gly Ala
                245                 250                 255

Ile Lys Glu Asp Leu Ser His Asn Ala Val Phe Ser Leu Pro Ile Thr
            260                 265                 270

Ser Pro Gly Pro Gly Glu Pro Val Gly Ile Ile Thr Arg Thr Gly Asp
        275                 280                 285

Thr Leu Ser Leu Ser Ala Glu Val Leu Met Ser Thr Ile Arg Lys Phe
    290                 295                 300

His Ser
305

<210> SEQ ID NO 15
<211> LENGTH: 80
<212> TYPE: DNA
<213> ORGANISM: Artificial sequence
<220> FEATURE:
<223> OTHER INFORMATION: primer

<400> SEQUENCE: 15
atggataggg tttcccggtt tagtcagcgc gtgcgcgtgc gccatcttca tgaagcctgc      60 tttttttatac taagttggca                                                 80

<210> SEQ ID NO 16
<211> LENGTH: 80
<212> TYPE: DNA
<213> ORGANISM: Artificial sequence
<220> FEATURE:
<223> OTHER INFORMATION: primer

<400> SEQUENCE: 16
gacaggcacg tccagcaccc gttgccgcaa ggccgccacc agctgcagct cgctcaagtt      60
agtataaaaa agctgaacga                                                  80

<210> SEQ ID NO 17
<211> LENGTH: 22
<212> TYPE: DNA
<213> ORGANISM: Artificial sequence
<220> FEATURE:
<223> OTHER INFORMATION: primer

<400> SEQUENCE: 17
acaatgtcct tgccgcttcg gc                                               22
```

<210> SEQ ID NO 18
<211> LENGTH: 22
<212> TYPE: DNA
<213> ORGANISM: Artificial sequence
<220> FEATURE:
<223> OTHER INFORMATION: primer

<400> SEQUENCE: 18
tgcattctgc gctctactgc gg                                              22

<210> SEQ ID NO 19
<211> LENGTH: 80
<212> TYPE: DNA
<213> ORGANISM: Artificial sequence
<220> FEATURE:
<223> OTHER INFORMATION: primer

<400> SEQUENCE: 19
atggaaaaaa atatccttt caatcagcgc attcgcttgc gtcatttaca tgaagcctgc       60 tttttatac taagttggca                                                   80

<210> SEQ ID NO 20
<211> LENGTH: 80
<212> TYPE: DNA
<213> ORGANISM: Artificial sequence
<220> FEATURE:
<223> OTHER INFORMATION: primer

<400> SEQUENCE: 20
ctgtgaaatt tacgaatagt actcatcaga acctcagcgc tcaggcttaa cgctcaagtt      60
agtataaaaa agctgaacga                                                  80

<210> SEQ ID NO 21
<211> LENGTH: 22
<212> TYPE: DNA
<213> ORGANISM: Artificial sequence
<220> FEATURE:
<223> OTHER INFORMATION: primer

<400> SEQUENCE: 21
cccgataaaa agtacacatt gt                                              22

<210> SEQ ID NO 22
<211> LENGTH: 22
<212> TYPE: DNA
<213> ORGANISM: Artificial sequence
<220> FEATURE:
<223> OTHER INFORMATION: primer

<400> SEQUENCE: 22
agttatctgg atcgttggct ac                                              22